US008114909B2

(12) United States Patent
Barrett et al.

(10) Patent No.: US 8,114,909 B2
(45) Date of Patent: Feb. 14, 2012

(54) TREATING OR PREVENTING RESTLESS LEGS SYNDROME USING PRODRUGS OF GABA ANALOGS

(75) Inventors: Ronald W. Barrett, Saratoga, CA (US); Daniel M. Canafax, Half Moon Bay, CA (US)

(73) Assignee: XenoPort, Inc., Santa Clara, CA (US)

( * ) Notice: Subject to any disclaimer, the term of this patent is extended or adjusted under 35 U.S.C. 154(b) by 571 days.

(21) Appl. No.: 10/969,196

(22) Filed: Sep. 17, 2004

(65) Prior Publication Data

US 2005/0192353 A1    Sep. 1, 2005

Related U.S. Application Data

(60) Provisional application No. 60/504,172, filed on Sep. 17, 2003, provisional application No. 60/504,726, filed on Sep. 18, 2003, provisional application No. 60/512,279, filed on Oct. 17, 2003, provisional application No. 60/538,495, filed on Jan. 22, 2004.

(51) Int. Cl.
*A01N 37/12* (2006.01)
*A01N 37/44* (2006.01)
*A61K 31/195* (2006.01)
*C07C 261/00* (2006.01)
*C07C 269/00* (2006.01)
*C07C 271/00* (2006.01)

(52) U.S. Cl. ........................................ 514/561; 560/115

(58) Field of Classification Search .......................... None
See application file for complete search history.

(56) References Cited

U.S. PATENT DOCUMENTS

| | | | |
|---|---|---|---|
| 2,996,431 A | 8/1961 | Barry |
| 3,139,383 A | 6/1964 | Neville |
| 3,402,240 A | 9/1968 | Cain et al. |
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,024,175 A | 5/1977 | Satzinger et al. |
| 4,063,064 A | 12/1977 | Saunders et al. |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,087,544 A | 5/1978 | Satzinger et al. |
| 4,088,864 A | 5/1978 | Theeuwes et al. |
| 4,093,709 A | 6/1978 | Choi et al. |
| 4,200,098 A | 4/1980 | Ayer et al. |
| 4,285,987 A | 8/1981 | Ayer et al. |
| 4,421,736 A | 12/1983 | Walters |
| 4,434,153 A | 2/1984 | Urquhart et al. |
| 4,721,613 A | 1/1988 | Urquhart et al. |
| 4,752,470 A | 6/1988 | Mehta |
| 4,816,263 A | 3/1989 | Ayer et al. |
| 4,820,523 A | 4/1989 | Shtohryn et al. |
| 4,853,229 A | 8/1989 | Theeuwes |
| 5,084,479 A | 1/1992 | Woodruff |
| 5,112,598 A | 5/1992 | Biesalski |
| 5,556,611 A | 9/1996 | Biesalski |
| 5,563,175 A | 10/1996 | Silverman et al. |
| 5,698,155 A | 12/1997 | Grosswald et al. |
| 5,707,663 A | 1/1998 | Ayer et al. |
| 6,001,876 A | 12/1999 | Singh |
| 6,020,370 A | 2/2000 | Horwell et al. |
| 6,024,977 A | 2/2000 | Yatvin et al. |
| 6,028,214 A | 2/2000 | Silverman et al. |
| 6,054,482 A | 4/2000 | Augart et al. |
| 6,103,932 A | 8/2000 | Horwell et al. |
| 6,117,906 A | 9/2000 | Silverman et al. |
| 6,171,615 B1 | 1/2001 | Roussin et al. |
| 6,310,098 B1 | 10/2001 | Guttuso |
| 6,375,987 B1 | 4/2002 | Farah et al. |
| 6,379,700 B2 | 4/2002 | Joachim et al. |
| 6,818,787 B2 * | 11/2004 | Gallop et al. ................. 560/115 |
| 6,833,140 B2 * | 12/2004 | Cundy et al. .................. 424/468 |
| 7,164,034 B2 * | 1/2007 | Dooley et al. ................. 554/108 |
| 2003/0144214 A1 | 7/2003 | Blakemore |
| 2003/0171303 A1 | 9/2003 | Gallop et al. |
| 2004/0077553 A1 | 4/2004 | Gallop et al. |
| 2005/0154057 A1 | 7/2005 | Estrada et al. |
| 2006/0141034 A1* | 6/2006 | Cundy et al. .................. 424/468 |
| 2010/0056632 A1 | 3/2010 | Estrada et al. |
| 2011/0021628 A1 | 1/2011 | Estrada et al. |

FOREIGN PATENT DOCUMENTS

| | | |
|---|---|---|
| EP | 1178034 A1 | 2/2002 |
| EP | 1201240 A2 | 5/2002 |
| EP | 1201240 A3 | 5/2002 |
| EP | 1003517 B1 | 6/2002 |
| GB | 2362646 A | 5/2000 |
| GB | 2362646 A | 11/2001 |
| WO | WO 92/09560 A1 | 6/1992 |
| WO | WO 93/23383 A1 | 11/1993 |
| WO | WO 97/29101 A1 | 8/1997 |
| WO | WO 97/33858 A1 | 9/1997 |

(Continued)

OTHER PUBLICATIONS

U.S. Appl. No. 10/966,507. U.S. Appl. No. 10/893,107.
Adler, "Treatment of restless legs syndrome with gabapentin," *Clin. Neuropharm.* 1997 (20:2)148-151.
Alderman, "A Review of cellulose Ethers in Hydrophilic Matrices dor Oral controlled-Release Dosage Forms," *Int. J. Pham. Tech. & Prod. Mfr.* 1984, 5(3) 1-9.
Bamba et al., "Release Mechanisms in Gelforming Sustained Release Preparations," *Int. J. Pharm.* 1979, 2, 307.
Bryans et al., "Identification of Novel Ligands for the Gabapentin binding Site $\alpha_2\delta$ Subunit of a Calcium Channel and Their Evaluation as Anitconvulsant Agents" *J. Med. Chem.* 1998, 41, 1838-1845.
Bryans et al., "3-Substituted GABA Analogs with Central Nervous System Activity: A Review," *Med. Res. Rev.* 1999, 19, 149-177.
Clark, "Restless legs syndrome," *J. Am. Fam. Prac.* 2001 (14:3) 368-374.

(Continued)

*Primary Examiner* — Marcela M Cordero Garcia

(74) *Attorney, Agent, or Firm* — Dorsey & Whitney LLP

(57) ABSTRACT

Disclosed herein are methods of using prodrugs of gamma aminobutyric acid (GABA) analogs and pharmaceutical compositions thereof to treat or prevent restless legs syndrome in humans, and pharmaceutical compositions of prodrugs of GABA analogs useful in treating or preventing restless legs syndrome.

52 Claims, No Drawings

FOREIGN PATENT DOCUMENTS

| | | |
|---|---|---|
| WO | WO 97-33859 A1 | 9/1997 |
| WO | WO 97/33859 A1 | 9/1997 |
| WO | WO 98/17627 A1 | 4/1998 |
| WO | WO 98/39005 A1 | 9/1998 |
| WO | WO 99/08671 A1 | 2/1999 |
| WO | WO 99/21824 A1 | 5/1999 |
| WO | WO 49/31074 A2 | 6/1999 |
| WO | WO 99/31057 A1 | 6/1999 |
| WO | WO 99/31074 A2 | 6/1999 |
| WO | WO 99/31074 A3 | 6/1999 |
| WO | WO 99/31075 A1 | 6/1999 |
| WO | WO 99/37296 A1 | 7/1999 |
| WO | WO 99/48484 A2 | 9/1999 |
| WO | WO 99/61424 A1 | 12/1999 |
| WO | WO 99/64213 A1 | 12/1999 |
| WO | WO 00/15611 A1 | 3/2000 |
| WO | WO 00/23067 A1 | 4/2000 |
| WO | WO 00/31020 A1 | 6/2000 |
| WO | WO 00/50027 A1 | 8/2000 |
| WO | WO 01/62290 A2 | 8/2001 |
| WO | WO 01/90052 A1 | 11/2001 |
| WO | WO 02/00209 A2 | 1/2002 |
| WO | WO 02/00209 A3 | 1/2002 |
| WO | WO 02/15889 A1 | 2/2002 |
| WO | WO 02/28411 A1 | 4/2002 |
| WO | WO 02/28881 A1 | 4/2002 |
| WO | WO 02/28883 A1 | 4/2002 |
| WO | WO 02/32376 A2 | 4/2002 |
| WO | WO 02/32376 A3 | 4/2002 |
| WO | WO 02/28883 A1 | 5/2002 |
| WO | WO 02/36123 A2 | 5/2002 |
| WO | WO 02/42414 A2 | 5/2002 |
| WO | WO 02/42414 A3 | 5/2002 |
| WO | WO 02/069974 A1 | 9/2002 |
| WO | WO 02/100344 A2 | 12/2002 |
| WO | WO 02/100344 A3 | 12/2002 |
| WO | WO 02/100347 A2 | 12/2002 |
| WO | WO 02/100347 A3 | 12/2002 |
| WO | WO 02/100349 A2 | 12/2002 |
| WO | WO 02/100349 A3 | 12/2002 |
| WO | WO 03/026676 A1 | 4/2003 |
| WO | WO 03/037329 A1 | 5/2003 |

OTHER PUBLICATIONS

Coleman et al., "Polymer Review: A Practical Guide to Polymer Miscibility," *Polymers* 1990, 31, 1187-1231.

During et al., "Controlled release of dopamine from a polymeric brain implant: in vivo characterization," 1989, *Ann. Neurol.* 25:351.

Ebrenberg et al., "Double-Blind Trial of Gabapentin for Periodic Limb Movement disorder of Sleep: Preliminary Results," *Neurology* 1998, 50:4, A276.

Ehrenberg et al., "Open-Label Trial of Gabapentin for Periodic Limb Movements Disorder of Sleep," *Neurology* 1997, 48:3, A278-279.

Fincher, "Particle Size of Drugs and Its Relationship to Absorption and Activity," *J. Pharm. Sci.* 1968, 57, 1825-1835.

Garcia-Borreguero et al., "Treatment of restless legs syndrome with gabapentin: A double-blind, cross-over study," *Neurology* 2002, 11:2, 1573-1579.

Gee et al., "The Novel Anticonvulsant Drug, Gabapentin (Neurontin), Binds to the $\alpha_2\delta$ of a Calcium Channel," *J. Biol. Chem.* 1996, 271, 5768-5776.

Greene et al. *Protective Groups in Organic Synthesis*, Wiley, 2$^{nd}$ Edition, (1991).

Hoes et al., "The Application of Drug-Polymer Conjugates in Chemotherapy," *Drug Carrier Systems* 1989, 9, 57-110.

Howard et al., "Intercerebral Drug Delivery in Rats with Lesion-Induced Memory Deficits," 1989, *J. Neurosurg.* 71:105-112.

Jezyk et al., "Transport of Pregabalin in Rat Intestine and Caco-2 Monolayers," *Pharm. Res.* 1999, 16, 519-526.

Langer et al., "Chemical and Physical Structure of Polymers as Carriers for Controlled Release of Bioactive Agents: A Review," *J Macromol. Sci. Rev. Macromol. Chem.* 1983, 23:61.

Leong et al., "Polymeric Controlled Drug Delivery," *Adv. Drug Delivery Rev.* 1987, 1, 199-233.

Levy et al., "Inhibition of Calcification of Bioprosthetic Heart Valves by Local Controlled-Release Diphosphonate,"*Science* 1985 228: 190.

Linhardt, *Controlled Release of Drugs: Polymers and Aggregate Systems* Chap. 2, (1989) pp. 53-95.

Lu, "Dimensionless Presentation for Drug Release From a Coated Pure Drug Bead: 2 Experiment," *Int. J. Pharm.*, 1994, 112, 117-124.

Magnus, "Nonepileptic Uses of Gabapentin," *Epilepsia*, (40) (Suppl. 6): S66-S72 (1999).

Mellick et al., "Management of restless legs syndrome with gabapentin (Neurontin)," *Sleep* 1996, 19:3, 224-226.

National Institutes of Health, 2003 National Sleep Disorders Research Plan, pp. 76-79.

Saudek et al., "A Preliminary Trial of the Programmable Implantable Medication System for Insulin Delivery," *N. Engl. J. Med.*, 1989, 321: 574.

Schaefer et al., "Gabapentin increases slow-wave sleep in normal adults," *Epilepsia* 2002 (43:12) 1493-1497.

Verma et al., "Osmotically Controlled Oral Drug Delivery," *Drug Dev. Ind. Pharm.*, 2000, 26:695-708.

Adler, Charles "Treatment of Restless Legs Syndrome with Gabapentin," *Clinical Neuropharmacology*, vol. 20, No. 2, pp. 148-151, 1997, Lippincott-Raven Publishers, Philadelphia.

XP13512 improves symptoms in moderate to severe restless legs syndrome in a 2 week randomized double-blind, placebo controlled, exploratory trial, *American College of Clinical Pharmacy 2006 Annual Meeting* Oct. 26-29, 2006 St Louis, Missouri.

Cochran, J. W. et al., "Restless Legs Syndrome", letter to *The Journal of the American Medical Association*, Jan. 17, 1996, vol. 275, No. 3.

"Restless Legs Syndrome (RLS): the continuing development of diagnostic standards and severity measures," 2003 Elsevier Science B. V.

ECDEU Assessment Manual, U. S. Dept of Health, Education and Welfare, Alcohol, Drug Abuse and Mental Health Administration.

Garcia-Borreguero, D. et al., "Treatment of restless legs syndrome with gabapentin, a double blind, cross-over study," Copyright Lippincott Williams and Wilkins 2002.

Kushida, C. et al., "XP13512 is Well Tolerated and Effective in Treating Moderate to Severe Restless Legs Syndrome in a 2 week Randomized Double-Blind, Placebo Controlled, Exploratory Trial".

Shargel, L. et al. *Applied Biopharmaceutics & Pharmacokinetics*, Fifth Edition, McGraw-Hill Medical Publishing Division pp. 768-769 (1995).

Thorp, M. et al., "A Crossover Study of Gabapentin in Treatment of Restless Legs Syndrome Among Hemodialysis Patients," *American Journal of Kidney Diseases*, vol. 38, No. 1 Jul. 2001 pp. 104-108.

"Gabapentin RLS Patient Studies", Xenoport, Inc. (Internal document).

Xenoport, Inc. Press Release—"Potential Treatment for RLS With a Different Mechanism of Action" Apr. 25, 2007.

"Validation of the International Restless Legs Syndrome Study Group rating scale for restless legs syndrome", The International Restless Legs Study Group, *Sleep Medicine 4*, (2003) 121-132.

Hening, W.A. et al., "Restless Legs Syndrome (RLS): the continuing development of diagnostic standards and severity measures," 2003 Elsevier Science B. V.

Kushida, C. et al., XP13512 improves symptoms in moderate to severe restless legs syndrome in a 2 week randomized double-blind, placebo controlled, exploratory trial, *American College of Clinical Pharmacy 2006 Annual Meeting* Oct. 26-29, 2006 St Louis, Missouri.

Mellick, G. A. et al., Letter to the Editor "Management of Restless Legs Syndrome with Gabapentin", 1996 *Sleep*, 19(3):224-226, American Sleep Disorders Association and Sleep Research Society.

Walters, et al., "Toward a Better Definition of the Restless Legs Syndrome," *Movement Disorders* 10(5): 634-642 (1995).

Walters, et al. "Validation of the International Restless Legs Syndrome Study Group rating scale for restless legs syndrome", The International Restless Legs Study Group, *Sleep Medicine 4*, (2003) 121-132.

U.S. Appl. No. 60/606,637, filed Aug. 13, 2004, Gallop et al.

Alderman, "A Review of Cellulose Ethers in Hydrophilic Matrices or Oral Controlled-Release Dosage Forms," *Int. J. Pharm. Tech. & Prod. Mfr.* 1984, 5 (3) 1-9.

Bamba et al, "Release Mechanisms in Gelforming Sustained Release Preparations," *Int. J. Pharm.* 1979, 2, 307.

During et al, "Controlled Release of Dopamine From a Polymeric Brain Implant: In Vivo Characterization,"1989, *Ann. Neurol.* 25:351.

Goodson, "Medical Applications of Controlled Release," vol. 2, pp. 115-138 (1984).

Howard et al, "Intercerebral Drug Delivery in Rats with Lesion-Induced Memory Deficits," 1989, *J. Neurosurg.* 71:105-112.

Kushida et al., XP13512 improves symptoms in moderate to severe restless legs syndrome in a 2 week randomized double-blind, placebo controlled exploratory trial. American College of Clinical Pharmacy (ACCP) 2006 Annual meeting, Oct. 26-29, 2006, St. Louis MO.

Langer, et al, "Chemical and Physical Structure of Polymers as Carriers for Controlled Release of Bioactive Agents: A Review," *J Macromol. Sci. Rev. Macromol Chem.* 1983, 23:61.

Langer, "New Method of Drug Delivery," 1990, *Science* 249:1527-1533.

Levy et al, "Inhibition of Calcification of Bioprosthetic Heart Valves by Local Controlled-Release Diphosphonate," *Science* 1985 228: 190-192.

Saudek et al, "A Preliminary Trial of the Programmable Implantable Medication System for Insulin Delivery," *New England Journal of Medicine and Surgery*, 1989, 31, 574-578.

Sefton, "Implantable Pumps," *CRC Crit Ref Biomed. Eng.* 1987, 14:201.

Verma et al, "Osmotically Controlled Oral Drug Delivery," *Drug Dev. Ind. Pharm.*, 2000, 26:695-708.

XenoPort, Inc. press release, XenoPort and GlaxoSmithKline report positive top-line results of final pivotal trial of XP13512/ GSK1838262 for restless legs syndrome, Apr. 25, 2007.

Preliminary Amendment, U.S. Appl. No. 10/966,507, 3 pages, Feb. 14, 2005.

Non-Final Office Action, U.S. Appl. No. 10/966,507, 6 pages, Jun. 21, 2007.

Response to Restriction Requirement, U.S. Appl. No. 10/966,507, 4 pages, Oct. 22, 2007.

Non-Final Office Action, U.S. Appl. No. 10/966,507, 5 pages, Oct. 29, 2007.

Amendment and Response to Non-Final Office Action, U.S. Appl. No. 10/966,507, 8 pages, Apr. 29, 2008.

Non-Final Office Action, U.S. Appl. No. 10/966,507, 8 pages, Jul. 23, 2008.

Interview Summary, U.S. Appl. No. 10/966,507, 2 pages, Aug. 7, 2008.

Non-Final Office Action, U.S. Appl. No. 10/966,507, 6 pages, Sep. 16, 2008.

Stevenson, Cheryl et al., Colonic Absorption of Antiepileptic Agents, Epilepsia, 38(1): pp. 63-37, 1997.

Rowland, Malcolm et al., Clinical Pharmacokinetics, Concepts and Applications, third edition, pp. 36-38, 55-56, 347, 1995.

Shargel, Leon et al., Introduction to Pharmacokinetics, Applied Biopharmaceutics and Pharmacokinetics, third edition, pp. 34-35, 465-469, 1993.

Kriel, Robert L. et al., Failure of Absorption of Gabapentin After Rectal Administration, Epilepsia, 38(11): 1242-1244, 1997.

Allen et al., Ansel's Pharmaceutical Dosage Forms and Drug Delivery Systems, Lippincott Williams & Wilkins, 8$^{th}$ Ed. (2005), pp. 153-160.

Alzet® Mini-osmotic Pump Model 2001D Specification Sheet, Durect Corp., Curpertino, CA, Feb. 2006 (2 pages).

Boyd et al., Effects of Age and Gender on Single-Dose Pharmacokinetics of Gabapentin, *Epilepsia*, 40:4 (1999), pp. 474-479.

Shargel et al., "Applied Biopharmaceutics & Pharmacokinetics", McGraw Hill, 5$^{th}$ Ed. (2005), pp. 8-9.

Shargel et al., "Applied Biopharmaceutics & Pharmacokinetics", McGraw Hill, 5$^{th}$ Ed. (2005), pp. 453-464.

Shargel et al., "Applied Biopharmaceutics & Pharmacokinetics", McGraw Hill, 5$^{th}$ Ed. (2005), pp. 591-593.

Wise et al., "Handbook of Pharmaceutical Controlled Release Technology", CRC Press (2000), p. 478.

Walters et al., Toward a better definition of the restless legs syndrome. *Movement Disorders* 1995, 10(5), 634-642.

Walters et al., Validation of the International Restless legs Syndrome Study Group rating scale for restless legs syndrome. *Sleep Medicine* 2003, 4, 121-132.

XenoPort, Inc. press release, XenoPort reports positive top-line phase 3 trial results of XP13512 in restless legs syndrome, Apr. 25, 2007.

XenoPort, Inc. press release, XenoPort and GlaxoSmithKline report positive top-line results of final pivotal trial of XP13512/ GSK1838262 for restless legs syndrome, Feb. 28, 2008.

Zhang, et al., Establishment of a spastic cerebral palsy model in rats, Chinese J of Clin Rehab, 2006, 10(3) 150-151.

Di Trapani et al., Gabapentin in the prophylaxis of migraine: a double-blind randomized placebo-controlled study. *Clin Ter*, 2000, 151(3):145-8.

Dunham and Miya, A note on a simple apparatus for detecting neurological deficit in rats and mice, *J Am Pharm Assoc Am Pharm Assoc.* 1957, 46(3):208-9.

Garcia-Borreguero et al., Treatment of restless legs syndrome with gabapentin, a double blind, cross-over study, *Neurology* 2002, 59, 1573-1579.

Gidal et al., Inter- and intra-subject variability in gabapentin absorption and absolute bioavailability. *Epilepsy Res* 2000, 40, 123-127.

Kushida et al., XP13512 improves symptoms and sleep disturbance in restless legs syndrome (RLS) patients: results of a 2 week, randomized, double blind, placebo controlled, crossover polysomnography trial. Sleep 2006: 20$^{th}$ Anniversary meeting of the Associated professional Sleep Societies (APSS), Salt lake City, Utah, Jun. 17-22, 2006, Abstract 172E.

Kushida et al., XP13512 is well tolerated and effective in treating moderate to severe restless legs syndrome in a 2 week randomized double-blind, placebo controlled exploratory trial. 58$^{th}$ Annual Meeting of the American Academy of Neurology (AAN), San Diego, CA, Apr. 1-8, 2006, Abstract 170E.

Lance et al., An electromyographic analysis of spasticity, *Trans Am Neurol Assoc.* 1970;95:272-4.

Magnus-Miller et al., Efficacy and safety of gabapentin (neurontin) in migraine prophylaxis [abstract]. Am Pain Soc Program, 17th Annual Meeting. 1998. Abstract 645.

McLean, Gabapentin. *Epilepsia* 1995, 36(Suppl 2), S73-S86.

Mellick et al., Management of restless legs syndrome with gabapentin. *Sleep* 1996, 19(3), 224-226.

Shargel et al., Applied Biopharmaceutics & Pharmacokinetics, 5$^{th}$ Ed., 1995, McGraw-Hill Medical Publishing Division, pp. 768-769.

Shargel et al., Applied Biopharmaceutics & Pharmacokinetics, 5$^{th}$ Ed., 1995, McGraw-Hill Medical Publishing Division, Chapter 19, pp. 575-611.

Stewart et al., A saturable transport mechanism in the intestinal absorption of gabapentin is the underlying cause of the lack of proportionality between increasing dose and drug levels in plasma. *Pharm Res* 1993, 10(2), 276-281.

Terrence et al., Effect of Baclofen Enantiomorphs on the Spinal Trigeminal Nucleus and Steric Similarities of Carbamazepine, *Pharm.*, 1983, 27, 85-94.

Thorp et al., A crossover study of gabapentin in treatment of restless legs syndrome among hemodialysis patients, *Am J Kidney Diseases* 2001, 38(1), 104-108.

Uchino et al., Transport of amino acid-related compounds mediated by L-type amino acid transporter 1 (LAT1): insights into the mechanisms of substrate recognition. *Mol Pharmacol* 2002, 61, 729-737.

Adler, Treatment of restless legs syndrome with gabapentin, *Clinical Neuropharmacology* 1997, 20(2), 148-151.

Canafax et al., Single- and multi-dose phase 1 studies of XP13512, a transported prodrug of gabapentin, demonstrate safety, tolerability, and dose-proportional gabapentin pharmacokinetics. 7$^{th}$ International Conference on the mechanisms and Treatment of Neuropathic Pain, Bermuda, Nov. 4-6, 2004.

Canafax et al., XP13512 improves symptoms in moderate to severe restless legs syndrome in a 2 week randomized double-blind, placebo controlled exploratory trial. American College of Clinical Pharmacy (ACCP) 2006 Annual meeting, Oct. 26-29, 2006, St. Louis MO.

Capuano et al., Antiepileptic drugs in migraine prophylaxis: state of the art, *Clin Ter.* 155 (2-3):79-87.

Cochran et al., Restless legs syndrome, *J Am Med Assoc* 1996, 275(3), 187.

Cooper et al., L-dopa esters as potential prodrugs: behavioural activity in experimental models of Parkinson's disease, *J Pharm Pharmacol.* 1987 39(8):627-35.

Cundy et al., Clinical pharmacokinetics of XP13512, a novel transported prodrug of gabapentin, 65th American Academy of Neurology Annual Meeting, Chicago, Il, Apr. 12-19, 2008.

Cundy et al., XP13512 [(±)-1-([(α-isobutanoyloxyethoxy)carbonyl]aminomethyl)—1-cyclohexane acetic acid], a novel gabapentin prodrug: II. Improved oral bioavailability, dose proportionality, and colonic absorption compared with gabapentin in rats and monkeys. *J Pharmacology and Experimental Therapeutics* 2004, 311(1), 324-333.

U.S. Appl. No. 60/511,287, filed Oct. 14, 2003, Estrada et al.
U.S. Appl. No. 10/966,507, filed Oct. 14, 2004, Estrada et al.
U.S. Appl. No. 12/548,200, filed Aug. 26, 2009, Estrada et al.
U.S. Appl. No. 12/897,567, filed Oct. 4, 2010, Estrada et al.

Garcia-Borreguero et al., Pregabalin in restless legs syndrome: A double-blind, placebo-controlled study with clinical and polysomnographic assessment, Pregabalin for RLS (AAN 2009), LB1.002, Feb. 25, 2009.

Goodman, Pregabalin Reported to Improve Restless Legs Symptoms and Sleep, Neurology Today (Jun. 4, 2009), 9(11), pp. 25,27, doi: 10.1097/01.NT.0000354551.40311.ab.

Happe et al., "Treatment of Idiopathic Restless :Legs Syndrome (RLS) With Gabapentin", Neurology:57, 2001, pp. 1717-1719.

XP060: XenoPort and GlaxoSmithKline Report positive top line results of second phase 3 Restless Legs Syndrome Trial for XP13512/XP1838262—Study highlights safety and efficacy of XP13512 in primary Restless Legs Syndrome patients treated for nine months; Press Release; Jan. 16, 2008.

GlaxoSmithKline Report and XenoPort Receive FDA Approval for Horizant™—New treatment for moderate-to-severe primary Restless Legs Syndrome; Press Release ; Apr. 6, 2011.

Winkelman et al., Randomized Polysomnography Study of Gabapentin Enacarbil in Subjects with Restless Legs Syndrome, *Movement Disorders* (2011).

Restriction Requirement dated Jun. 21, 2007, U.S. Appl. No. 10/966,507, 6 pages.
Response to Election Requirement dated Oct. 22, 2007, U.S. Appl. No. 10/966,507, 4 pages.
Office Action dated Oct. 29, 2007, U.S. Appl. No. 10/966,507, 9 pages.
Response to Office Action dated Apr. 29, 2008, U.S. Appl. No. 10/966,507, 12 pages.
Final Office Action dated Jul. 23, 2008, U.S. Appl. No. 10/966,507, 10 pages.
Interview Summary filed Aug. 7, 2008, U.S. Appl. No. 10/966,507, 2 pages.
Office Action dated Sep. 16, 2008, U.S. Appl. No. 10/966,507, 6 pages.
Response to Office Action dated Dec. 16, 2008, U.S. Appl. No. 10/966,507, 9 pages.
Final Office Action dated Apr. 7, 2009, U.S. Appl. No. 10/966,507, 13 pages.
Response to Final Office Action with RCE dated Jul. 14, 2009, U.S. Appl. No. 10/966,507, 13 pages.
Office Action dated Jul. 24, 2009, U.S. Appl. No. 10/966,507, 9 pages.
Response to Office Action dated Jan. 22, 2010, U.S. Appl. No. 10/966,507, 24 pages.
Final Office Action dated Apr. 16, 2010, U.S. Appl. No. 10/966,507, 9 pages.
Notice of Appeal dated Oct. 15, 2010, U.S. Appl. No. 10/966,507, pages.
Response to Final Office Action with RCE dated Apr. 13, 2011, U.S. Appl. No. 10/966,507, 18 pages.
Notice of Allowance and Interview summary dated Sep. 7, 2010, U.S. Appl. No. 10/966,507, 12 pages.
Office Action dated Apr. 2, 2010, U.S. Appl. No. 12/548,200, 18 pages.
Office Action dated Dec. 20, 2010, U.S. Appl. No. 12/897,567, 26 pages.
Walters et al., "Gabapentin Enacarbil in Restless Legs Syndrome: A Phase 2b, Two-Week, Randomized, Double-Blind, Placebo-Controlled Trial," Clin. Neuropharmacol., Nov.-Dec. 2009, 32(6):311-20.

\* cited by examiner

TREATING OR PREVENTING RESTLESS LEGS SYNDROME USING PRODRUGS OF GABA ANALOGS

This application claims priority under 35 U.S.C. §119 (e) from U.S. Provisional Application Ser. Nos. 60/504,172, 60/504,726, 60/512,279 and 60/538,495, filed on Sep. 17, 2003, Sep. 18, 2003, Oct. 17, 2003 and Jan. 22, 2004, respectively.

1. TECHNICAL FIELD

The methods and compositions disclosed herein relate generally to treating or preventing restless legs syndrome in a patient. More specifically, disclosed herein are methods of using prodrugs of GABA analogs and pharmaceutical compositions thereof to treat or prevent restless legs syndrome in patients and pharmaceutical compositions of prodrugs of GABA analogs useful in treating or preventing restless legs syndrome.

2. BACKGROUND

Restless legs syndrome (RLS) afflicts between 5 and 10% of the general population. Although the clinical origin of RLS is unknown, four characteristic symptoms of RLS exist: 1) lower extremity dysesthesias or paresthesias; 2) motor restlessness; 3) nocturnal increase of paresthesias and motor restlessness; and 4) symptoms that increase at rest, i.e., sitting or lying. Typically, symptoms increase at night (Garcia-Borreguero et al., *Neurol.* 2002 (11:2) 1573-79). RLS may start at any age, even during childhood, although is usually observed in adults. The clinical course generally changes over time, but tends to become more pronounced with age, with up to 28% of those over 65 being affected (Clark, *J. Am. Fam. Prac.* 2001 (14:3) 368-374).

RLS is an intensely uncomfortable sensory-motor disorder. Besides sensory symptoms such as paresthesia, which is a sensation of numbness, tingling, burning or pain, accompanied by an urge to move the limbs, patients also experience motor symptoms. When awake and sitting or lying down, the patient may exhibit rhythmic or semi-rhythmic movements of the legs (i.e., dysesthesias). While sleeping, patients frequently demonstrate similar semi-rhythmic legs movements, which have been referred to as periodic leg movements during sleep (PLMS). These jerky leg movements are repetitive, highly stereotypical and are characterized by extension of the big toe along with flexion of the ankle, knee and sometimes the hip (i.e., a Babinski-like movement) (Clark, supra). About 85-90% of RLS sufferers also exhibit PLMS and these patients complain of daytime fatigue and sleepiness or insomnia which have a profound negative effect on quality of life, including daytime fatigue, poor work performance and interrupted social and/or family life (National Institutes of Health, 2003 *National Sleep Disorders Research Plan*, pp. 76-79).

The origin of RLS and PLMS is unknown and most cases are classified as idiopathic. Clinical and laboratory findings suggest that the dopaminergic neurotransmitter system may be involved. Defects in the opioid and serotonin systems may also play a role (Adler, *Clin. Neuropharm.* 1997 (20:2) 148-151). RLS is more prevalent in women than men and in individuals of Northern European ancestry. The inheritance pattern of RLS suggests an autosomal dominant mode of transmittance, but the genes accounting for this observation are not known (N.I.H., 2003).

Certain patient populations exhibit RLS more frequently than does the general population. In particular, iron deficiency has been associated with RLS, as have decreased levels of magnesium and folate. Dialysis patients, perhaps because of the prevalence of associated anemia, are frequently afflicted, with 20% to 57% having symptoms of RLS. In addition, pregnant women often complain of RLS, although symptoms usually diminish or disappear after delivery (Clark, supra).

RLS and RLS with PLMS are currently treated with dopaminergic drugs, such as L-dopa, bromocriptine, pergolide, pramipexole or ropinirole. However, dopaminergic drugs have a poor side-effects profile, most notably, causing nausea. In addition, many dopaminergic drugs exhibit a rebound phenomenon, in which symptoms tend to increase as a dose diminishes, such that the patient experiences disruptive problems during the night or early morning. Further, a phenomenon known as augmentation (i.e., patients experience relief of night-time symptoms, but day-time symptoms increase and may spread to other parts of the body, such as the arms) occurs in a majority of patients on long-term dopaminergic therapy. Opiates such as codeine, tramadol, oxycodone and propoxyphene have also been used to treat RLS. The addictiveness of opiates limits use of these narcotics to treat or prevent RLS to severely afflicted patients. Benzodiazepines, particularly clonazepam, are also used to treat mild and sleep-related cases of RLS (Clark, supra). Again, side effects such as daytime drowsiness, confusion and unsteadiness limit the use of benzodiazepines to treat or prevent RLS. In addition, some patients with RLS are refractory to treatment with any current medical therapy.

The γ-aminobutyric acid (γ-aminobutyric acid is abbreviated herein as "GABA") analog gabapentin (1) has been approved in the United States for the treatment of epileptic seizures and post-herpetic neuralgia. The drug has also shown efficacy in controlled studies for treating neuropathic pain of varying etiologies. Gabapentin has been used to treat a number of other medical disorders (Magnus, *Epilepsia* 1999, 40, S66-72). In addition, gabapentin has shown utility in treating restless legs syndrome (Mellick et al., *Sleep* 1996, 19:3, 224-226; Adler, *Clin. Neuropharm.* 1997, 20:2, 148-151; Ehrenberg et al., *Neurol.* 1997, 48:3, A278-279; Ehrenberg et al., *Neurology* 1998, 50:4, A276; Garcia-Borreguero et al., *Neurology* 2002, 11:2, 1573-79).

The broad pharmaceutical activities of GABA analogs such as gabapentin has

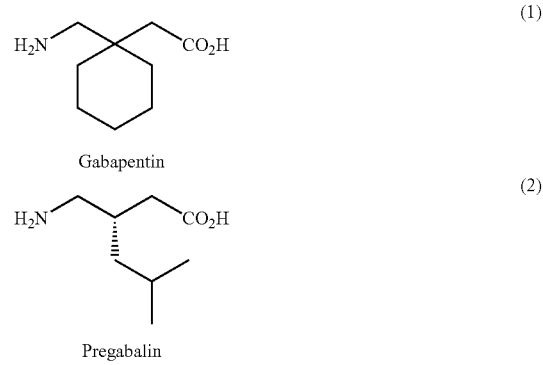

stimulated intensive interest in preparing related compounds that have superior pharmaceutical properties in comparison to GABA, e.g., the ability to cross the blood brain barrier (see, e.g., Satzinger et al., U.S. Pat. No. 4,024,175; Silverman et al, U.S. Pat. No. 5,563,175; Horwell et al., U.S. Pat. No. 6,020, 370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101; Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Belliotti et al., International Publication No. WO 99/31074; Bryans et al., International Publication No. WO 99/31075; Bryans et al., International Publication No. WO 99/61424; Bryans et al., International Publication No. WO 00/15611; Belliotti et al., International Publication No. WO 00/31020; Bryans et al., International Publication No. WO 00/50027; and Bryans et al., International Publication No. WO 02/00209). A number of the above documents disclose the use of gabapentin analogs for the treatment of neuropathic pain states. One analog of particular interest is pregabalin (2), which may possess greater potency in pre-clinical models of pain and epilepsy than gabapentin.

Although the mechanism of action of gabapentin in modulating these aforementioned disease states (including restless leg syndrome) is not understood with certainty, gabapentin, pregabalin and related analogs are known to interact with the $\alpha_2\delta$ subunit of neuronal voltage-gated calcium channels (Gee et al., *J. Biol. Chem.* 1996, 271, 5768-5776; Bryans et al., *J. Med. Chem.* 1998, 41, 1838-1845). A method of administering a compound to a patient which binds an $\alpha_2\delta$ subunit of a voltage-gated calcium channel has been described. Preferred compounds include the GABA analogs gabapentin and pregabalin (Guttuso, U.S. Pat. No. 6,310,098).

One significant problem associated with the clinical use of many GABA analogs, including gabapentin and pregabalin, is rapid systemic clearance. Consequently, these drugs require frequent dosing to maintain a therapeutic or prophylactic concentration in the systemic circulation (Bryans et al., *Med. Res. Rev.* 1999, 19, 149-177). For example, dosing regimens of 300-600 mg doses of gabapentin administered three times per day are typically used for anticonvulsive therapy. Higher doses (1800-3600 mg/day in three or four divided doses) are typically used for the treatment of neuropathic pain states.

Although oral sustained released formulations are conventionally used to reduce the dosing frequency of drugs that exhibit rapid systemic clearance, oral sustained release formulations of gabapentin and pregabalin have not been developed because these drugs not absorbed via the large intestine. Rather, these compounds are typically absorbed in the small intestine by one or more amino acid transporters (e.g., the "large neutral amino acid transporter," see Jezyk et al., *Pharm. Res.* 1999, 16, 519-526). The limited residence time of both conventional and sustained release oral dosage forms in the proximal absorptive region of the gastrointestinal tract necessitates frequent daily dosing of conventional oral dosage forms of these drugs, and has prevented the successful application of sustained release technologies to many GABA analogs.

One method for overcoming rapid systemic clearance of GABA analogs relies upon the administration of an extended release dosage formulation containing a GABA analog prodrug (Gallop et al., International Publication Nos. WO 02/100347 and WO 02/100349). Such prodrugs may be absorbed over wider regions of the gastrointestinal tract than the parent drug, and across the wall of the colon where sustained release oral dosage forms typically spend a significant portion of gastrointestinal transit time. These prodrugs are typically converted to the parent GABA analog upon absorption in vivo.

Current therapeutic agents for RLS either have significant side effects or are rapidly systemically cleared. Therefore, there is a need in the art for a method of delivering an agent, such as a prodrug of a GABA analog, particularly in extended release dosage forms, with reduced rates of systemic clearance which can also treat or prevent RLS without significant side effects.

3. SUMMARY

Methods of treating or preventing restless legs syndrome in a patient are disclosed herein. The methods find use in treating or preventing restless legs syndrome characterized by symptoms while the patient is inactive during the day and/or while sleeping.

In one aspect, a method of treating or preventing RLS, in a patient which comprises administering to the patient a therapeutically effective amount of a prodrug of a GABA analog or a pharmaceutically acceptable salt, hydrate, solvate or N-oxide thereof is provided. The method finds use in patients suffering from idiopathic RLS as well as patients in which RLS results from secondary causes such as iron deficiency.

In other embodiments, a method is provided for improving sleep quality in a patient suffering from RLS, which comprises administering to the patient a therapeutically effective amount of a prodrug of a GABA analog or a pharmaceutically acceptable salt, hydrate, solvate or N-oxide thereof.

In a second aspect, a method of treating or preventing RLS in a patient comprising administering to the patient a pharmaceutical composition which comprises a therapeutically effective amount of a prodrug of a GABA analog or a pharmaceutically acceptable salt, hydrate, solvate or N-oxide thereof and a pharmaceutically acceptable vehicle is provided.

Methods disclosed herein are not restricted to particular prodrugs of GABA analogs. Accordingly, the disclosed methods may be practiced with any GABA analog prodrug. In some embodiments, GABA analog prodrugs which bind the $\alpha_2\delta$ subunit of a voltage-gated calcium channel, such as prodrugs of gabapentin and pregabalin are used to treat or prevent RLS.

In other embodiments, a prodrug of a GABA analog has the structure of Formula (I):

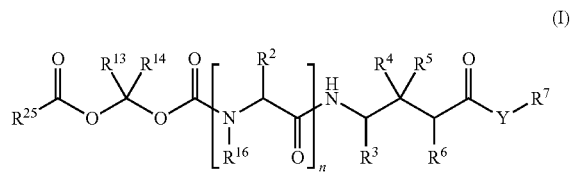

or a pharmaceutically acceptable salt, hydrate, solvate or N-oxide thereof, wherein:

n is 0 or 1;

Y is O or S;

$R^{16}$ is hydrogen, alkyl or substituted alkyl;

$R^2$ is selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, or optionally, $R^2$ and $R^{16}$ together with the atoms to which they are attached form a cycloheteroalkyl or substituted cycloheteroalkyl ring;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl or optionally, $R^4$ and $R^5$ together with the carbon atom to which they are attached form a cycloalkyl, substituted cycloalkyl, cycloheteroalkyl, substituted cycloheteroalkyl or bridged cycloalkyl ring;

$R^7$ is selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{13}$ and $R^{14}$ are each independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroaryl, substituted heteroaryl, heteroarylalkyl or substituted heteroarylalkyl or optionally, $R^{13}$ and $R^{14}$ together with the carbon atom to which they are attached form a cycloalkyl, substituted cycloalkyl, cycloheteroalkyl or substituted cycloheteroalkyl ring; and $R^{25}$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

In a third aspect, a pharmaceutical composition for treating a patient suffering from RLS is provided. The pharmaceutical composition comprises a therapeutically effective amount of a prodrug of a GABA analog or a pharmaceutically acceptable salt, hydrate, solvate or N-oxide thereof and a pharmaceutically acceptable vehicle.

In a fourth aspect, a pharmaceutical composition for preventing RLS in a patient at a risk of RLS is provided. The pharmaceutical composition comprises a therapeutically effective amount of a prodrug of a GABA analog or a pharmaceutically acceptable salt, hydrate, solvate or N-oxide thereof and a pharmaceutically acceptable vehicle.

4. DETAILED DESCRIPTION

4.1 Definitions

"Compounds" refers to GABA analogs and prodrugs of GABA analogs including any compounds encompassed by generic formulae disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. Compounds may also exist in several tautomeric forms including the enol form, the keto form and mixtures thereof. Accordingly, the chemical structures depicted herein encompass all possible tautomeric forms of the illustrated compounds. Compounds described herein also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. All physical forms are equivalent for the uses contemplated herein. Further, it should be understood, when partial structures of the compounds are illustrated, that brackets indicate the point of attachment of the partial structure to the rest of the molecule.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms. $(C_1-C_6)$alkyl, for example, refers to an alkyl group containing from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{32}$ where R$^{32}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably from 6 to 12 carbon atoms.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is (C$_6$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$), more preferably, an arylalkyl group is (C$_6$-C$_{20}$)arylalkyl, e.g., the alkanyl, alkenyl or alkynyl moiety of the arylalkyl group is (C$_1$-C$_8$) and the aryl moiety is (C$_6$-C$_{12}$).

"AUC" is the area under the plasma drug concentration-versus-time curve extrapolated from zero time to infinity.

"Bridged cycloalkyl" refers to a radical selected from the group consisting of

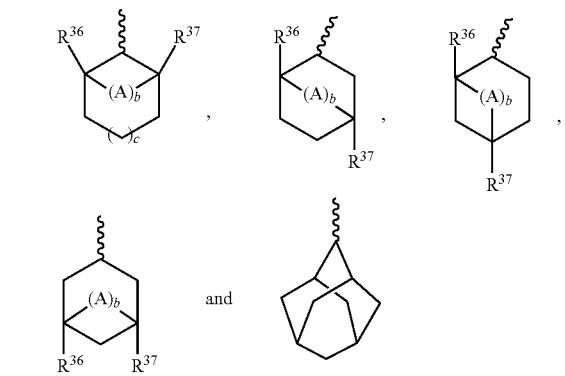

wherein:

A is (CR$^{38}$R$^{39}$)$_b$;

R$^{38}$ and R$^{39}$ are independently selected from the group consisting of hydrogen and methyl;

R$^{36}$ and R$^{37}$ are independently selected from the group consisting of hydrogen and methyl;

b is an integer from 1 to 4; and c is an integer from 0 to 2.

"Carbamoyl" by itself or as part of another substituent refers to the radical —C(O)NR$^{40}$R$^{41}$ where R$^{40}$ and R$^{41}$ are independently hydrogen, alkyl, cycloalkyl or aryl as defined herein.

"C$_{max}$" is the highest drug concentration observed in plasma following an extravascular dose of drug.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. Preferably, the cycloalkyl group is (C$_3$-C$_{10}$)cycloalkyl, more preferably (C$_3$-C$_7$)cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"GABA analog" refers to a compound, unless specified otherwise, as having the following structure:

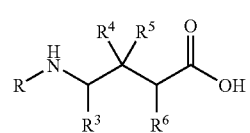

wherein:

R is hydrogen, or R and $R^6$ together with the atoms to which they are attached form an azetidine, substituted azetidine, pyrrolidine or substituted pyrrolidine ring;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl; and $R^4$ and $R^5$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl or optionally, $R^4$ and $R^5$ together with the carbon atom to which they are attached form a cycloalkyl, substituted cycloalkyl, cycloheteroalkyl, substituted cycloheteroalkyl or bridged cycloalkyl ring.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —$NR^{42}R^{43}$, —$N=N$—, —N=N—, —N=N—$NR^{44}R^{45}$, —$PR^{46}$—, —$P(O)_2$—, —$POR^{47}$—, —O—$P(O)_2$—, —SO—, —$SO_2$—, —$SnR^{48}R^{49}$— and the like, where $R^{42}$, $R^{43}$, $R^{44}$, $R^{45}$, $R^{46}$, $R^{47}$, $R^{48}$ and $R^{49}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine "Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl, more preferably, 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Improve", "improving" and "improvement" of sleep in patients suffering from restless legs syndrome all refer to making the subjective and/or objective measures of sleep quality better. As used herein, the term "improve" with respect to sleep, is meant to reduce, prevent (e.g., prophylaxis), reverse (e.g., alleviate), ameliorate, control or manage the sleeplessness and other symptoms associated with RLS.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indanie, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Patient" refers to a mammal, which is preferably human.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a GABA analog prodrug or other therapeutic compound disclosed herein is administered.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, enamine, imine, N-phosphonyl, N-phosphoryl or N-sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which have functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Restless legs syndrome" (RLS) refers to a movement disorder of unknown origin characterized by an irritating sensation of uneasiness, tiredness and itching deep within the muscles of the leg, accompanied by twitching and, occasionally, by pain. The condition is sometimes known as restlessness syndrome. Four characteristic symptoms of RLS exist: 1) lower extremity dysesthesias or paresthesias; 2) motor restlessness; 3) nocturnal increase of paresthesias and motor restlessness; and 4) symptoms that increase at rest, i.e., sitting or lying. Included in the definition of RLS are the related conditions periodic limb movement(s) disorder (PLMD) and periodic leg movements during sleep (PLMS), also designated herein as RLS with PLMS. RLS is also known as anxietas tibiarum, Ekbom syndrome and Wittmaack-Ekbom syndrome.

"Substituted" refers to a group in which one or more hydrogen atoms are independently replaced with the same or different substituent(s). Typical substituents include, but are not limited to, -M, $-R^{60}$, $-O^-$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$ and $-C(NR^{62})NR^{60}R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include -M, $-R^{60}$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-NR^{62}C(O)NR^6OR^{61}$, more preferably, -M, $-R^{60}$, $=O$, $-OR^{60}$, $-SR^{60}$, $-NR^{60}R^{61}$, $-CF_3$, $-CN$, $-NO_2$, $-S(O)_2R^{60}$, $-P(O)(OR^{60})(O^-)$, $-OP(O)(OR^{60})(OR^{61})$, $-C(O)R^{60}$, $-C(O)OR^{60}$, $-C(O)NR^{60}R^{61}$, $-C(O)O^-$, most preferably, -M, $-R^{60}$, $=O$, $-OR^{60}$, $-SR^{61}$, $-NR^{60}R^{61}$, $-CF_3$, $-CN$, $-NO_2$, $-S(O)_2R^{60}$, $-OP(O)(OR^{60})(OR^{61})$, $-C(O)R^{60}$, $-C(O)OR^{60}$, $-C(O)O^-$, where $R^{60}$, $R^{61}$ and $R^{62}$ are as defined above.

"Sustained release" refers to release of an agent from a dosage form at a rate effective to achieve a therapeutic or prophylactic amount of the agent, or active metabolite thereof, in the systemic blood circulation over a prolonged period of time relative to that achieved by oral administration of a conventional formulation of the agent. In some embodiments, release of the agent occurs over a period of at least 6 hours. In other embodiments, release of the agent occurs over a period of at least 8 hours. In still other embodiments, release of the agent occurs over a period of at least 12 hours.

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease.

The "therapeutically effective amount" will vary depending on the compound, the disease and its severity and the age, weight, etc., of the patient to be treated.

Reference will now be made in detail to preferred embodiments. It will be understood that the invention is not limited to those preferred embodiments. To the contrary, it is intended to cover alternatives, modifications, and equivalents as may be included within the spirit and scope of the allowed claims.

4.2 GABA Analog Prodrugs

In some embodiments, a prodrug of a GABA analog has the structure of Formula (I):

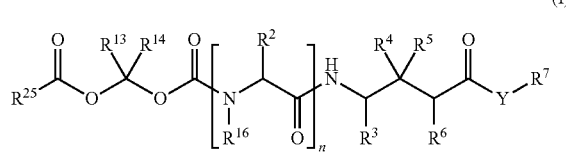

(I)

or a pharmaceutically acceptable salt, hydrate, solvate or N-oxide thereof, wherein:

n is 0 or 1;

Y is O or S;

$R^{16}$ is hydrogen, alkyl or substituted alkyl;

$R^2$ is selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, or optionally, $R^2$ and $R^{16}$ together with the atoms to which they are attached form a cycloheteroalkyl or substituted cycloheteroalkyl ring;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl or optionally, $R^4$ and $R^5$ together with the carbon atom to which they are attached form a cycloalkyl, substituted cycloalkyl, cycloheteroalkyl, substituted cycloheteroalkyl or bridged cycloalkyl ring;

$R^7$ is selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{13}$ and $R^{14}$ are each independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroaryl, substituted heteroaryl, heteroarylalkyl or substituted heteroarylalkyl or optionally, $R^{13}$ and $R^{14}$ together with the carbon atom to which they are attached form a cycloalkyl, substituted cycloalkyl, cycloheteroalkyl or substituted cycloheteroalkyl ring; and $R^{25}$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

In some embodiments, $R^{13}$ and $R^{14}$ are independently hydrogen, alkyl, substituted alkyl, alkoxycarbonyl, aryl, arylalkyl, carbamoyl, cycloalkyl, substituted cycloalkyl, or heteroaryl (preferably, when $R^{13}$ is alkoxycarbonyl or carbamoyl then $R^{14}$ is methyl). In other embodiments, $R^{13}$ and $R^{14}$ are independently hydrogen, methyl, ethyl, propyl, isopropyl, butyl, isobutyl, sec-butyl, tert-butyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl.

In still other embodiments, $R^{13}$ and $R^{14}$ are independently hydrogen, alkanyl, substituted alkanyl, cycloalkanyl or substituted cycloalkanyl. In still other embodiments, $R^{13}$ and $R^{14}$ are hydrogen, alkanyl or cycloalkanyl. In still other embodiments, $R^{13}$ and $R^{14}$ are independently hydrogen, methyl, ethyl, propyl, isopropyl, butyl, isobutyl, sec-butyl, tert-butyl, cyclopentyl or cyclohexyl. In still other embodiments, $R^{13}$ is methyl, ethyl, propyl, isopropyl, butyl, isobutyl, sec-butyl, tert-butyl, cyclopentyl or cyclohexyl and $R^{14}$ is hydrogen, or $R^{13}$ is methyl and $R^{14}$ is methyl.

In still other embodiments, $R^{13}$ and $R^{14}$ are independently hydrogen, aryl, arylalkyl or heteroaryl. In still other embodiments, $R^{13}$ and $R^{14}$ are independently hydrogen, phenyl, benzyl, phenethyl or 3-pyridyl. In still other embodiments, $R^{13}$ is phenyl, benzyl, phenethyl or 3-pyridyl and $R^{14}$ is hydrogen.

In still other embodiments, $R^{13}$ and $R^{14}$ are independently hydrogen, alkyl, substituted alkyl, alkoxycarbonyl or carbamoyl. In still other embodiments, $R^{13}$ is alkoxycarbonyl or carbamoyl and $R^{14}$ is methyl. In still other embodiments, $R^{13}$ is methoxycarbonyl, ethoxycarbonyl, isopropoxycarbonyl, butoxycarbonyl, isobutoxycarbonyl, sec-butoxycarbonyl, tert-butoxycarbonyl or cyclohexyloxycarbonyl and $R^{14}$ is methyl.

In still other embodiments, $R^{13}$ and $R^{14}$ together with the carbon atom to which they are attached form a cycloalkyl, substituted cycloalkyl, cycloheteroalkyl or substituted cycloheteroalkyl ring. In still other embodiments, $R^{13}$ and $R^{14}$ together with the carbon atom to which they are attached form a cycloalkyl ring. In still other embodiments, $R^{13}$ and $R^{14}$ together with the carbon atom to which they are attached form a cyclobutyl, cyclopentyl or cyclohexyl ring.

In still other embodiments of compounds of Formula (I), $R^{25}$ is acyl, substituted acyl, alkyl, substituted alkyl, aryl, arylalkyl, cycloalkyl or heteroaryl. In still other embodiments, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still other embodiments, $R^{25}$ is acyl or substituted acyl. In still other embodiments, $R^{25}$ is acetyl, propionyl, butyryl, benzoyl or phenacetyl.

In still other embodiments, $R^{25}$ is alkanyl or substituted alkanyl. In still other embodiments, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl or 1-(1,3-dioxan-2-yl)-2-phenethyl. In still other embodiments, $R^{25}$ is methyl, ethyl, propyl, isopropyl, butyl, 1,1-dimethoxyethyl or 1,1-diethoxyethyl.

In still other embodiments, $R^{25}$ is aryl, arylalkyl or heteroaryl. In still other embodiments, $R^{25}$ is phenyl, 4-methoxyphenyl, benzyl, phenethyl, styryl or 3-pyridyl.

In still other embodiments, $R^{25}$ is cycloalkyl or substituted cycloalkyl. In still other embodiments, $R^{25}$ is cyclopropyl, cyclobutyl, cyclopentyl or cyclohexyl.

In still other embodiments, $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, alkoxycarbonyl, aryl, arylalkyl, carbamoyl, cycloalkyl, or heteroaryl (preferably, $R^{13}$ is alkoxycarbonyl or carbamoyl and $R^{14}$ is methyl). In still other embodiments, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl and $R^{13}$ and $R^{14}$ are independently hydrogen, methyl, ethyl, propyl, isopropyl, butyl, isobutyl, sec-butyl, tert-butyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl. In still other embodiments, $R^{25}$ is methyl, ethyl, propyl, isopropyl, butyl, isobutyl, sec-butyl, 1,1-dimethoxyethyl, 1,1-diethoxyethyl, 1,1-dimethoxybenzyl, 1,1-diethoxybenzyl, 1,1-dimethoxy-2-phenethyl, 1,1-diethoxy-2-phenethyl, acetyl, propionyl, butyryl, benzoyl, phenacetyl, phenyl, 4-methoxyphenyl, benzyl, phenethyl, cyclohexyl or 3-pyridyl and $R^{13}$ and $R^{14}$ are independently hydrogen, methyl, ethyl, propyl, isopropyl, butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl or 3-pyridyl.

In still other embodiments, $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl and $R^{13}$ and $R^{14}$ together with the atom to which they are attached form a cycloalkyl, substituted cycloalkyl, cycloheteroalkyl or substituted cycloheteroalkyl ring. In still other embodiments, $R^{25}$ is acyl, substituted acyl, alkyl, substituted alkyl, aryl, arylalkyl, cycloalkyl or heteroaryl and $R^{13}$ and $R^{14}$ together with the atom to which they are attached form a cycloalkyl or substituted cycloalkyl ring. In still other embodiments, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl and $R^{13}$ and $R^{14}$ together with the atom to which they are attached form a cyclobutyl, cyclopentyl or a cyclohexyl ring.

In still other embodiments, $R^{25}$ is acyl or substituted acyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroaryl or substituted heteroaryl (preferably, when $R^{13}$ is alkoxycarbonyl, substituted alkoxycarbonyl, carbamoyl or substituted carbamoyl then $R^{14}$ is methyl). In still other embodiments, $R^{25}$ is acetyl, propionyl, butyryl, benzoyl or phenacetyl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroaryl or substituted heteroaryl (preferably, when $R^{13}$ is alkoxycarbonyl, or carbamoyl then $R^{14}$ is methyl).

In still other embodiments, $R^{25}$ is alkanyl or substituted alkanyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroaryl or substituted heteroaryl (preferably, when $R^{13}$ is alkoxycarbonyl, substituted alkoxycarbonyl, carbamoyl or substituted carbamoyl then $R^{14}$ is methyl). In still other embodiments, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl or 1-(1,3-dioxan-2-yl)-2-phenethyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroaryl or substituted heteroaryl (preferably, when $R^{13}$ is alkoxycarbonyl or carbamoyl then $R^{14}$ is methyl).

In still other embodiments, $R^{25}$ is aryl, substituted aryl, arylalkyl, substituted arylalkyl, heteroaryl or substituted heteroaryl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl or substituted heteroaryl (preferably, when $R^{13}$ is alkoxycarbonyl, substituted alkoxycarbonyl, carbamoyl or substituted carbamoyl then $R^{14}$ is methyl). In still other embodiments, $R^{25}$ is phenyl, 4-methoxyphenyl, benzyl, phenethyl, styryl or 3-pyridyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl or substituted heteroaryl (preferably, when $R^{13}$ is alkoxycarbonyl or carbamoyl then $R^{14}$ is methyl).

In still other embodiments, $R^{25}$ is cycloalkyl or substituted cycloalkyl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl or substituted heteroaryl (preferably, when $R^{13}$ is alkoxycarbonyl, substituted alkoxycarbonyl, carbamoyl or substituted carbamoyl then $R^{14}$ is methyl). Preferably, $R^{25}$ is cyclopropyl, cyclobutyl, cyclopentyl or cyclohexyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl or substituted heteroaryl (preferably, when $R^{13}$ is alkoxycarbonyl, or carbamoyl then $R^{14}$ is methyl).

In still other embodiments, $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, and $R^{13}$ and $R^{14}$ are independently hydrogen, alkyl, substituted alkyl, aryl, arylalkyl, cycloalkyl or heteroaryl. In still other embodiments, $R^{25}$ is acyl, substituted acyl, alkyl, substituted alkyl, aryl, arylalkyl, cycloalkyl or heteroaryl and $R^{13}$ and $R^{14}$ are independently hydrogen, alkanyl, substituted alkanyl, cycloalkanyl or substituted cycloalkanyl. In still other embodiments, $R^{25}$ is acyl, substituted acyl, alkyl, substituted alkyl, aryl, arylalkyl, cycloalkyl or heteroaryl and $R^{13}$ and $R^{14}$ are independently hydrogen, methyl, ethyl, propyl, isopropyl, butyl, isobutyl, sec-butyl, tert-butyl, cyclopentyl or cyclohexyl. In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still other embodiments, $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, aryl, arylalkyl, cycloalkyl or heteroaryl. In still other embodiments, $R^{25}$ is acyl, substituted acyl, alkyl, substituted alkyl, aryl, arylalkyl, cycloalkyl or heteroaryl and $R^{13}$ and $R^{14}$ are independently hydrogen, aryl, arylalkyl or heteroaryl. In still other embodiments, $R^{25}$ is acyl, substituted acyl, alkyl, substituted alkyl, aryl, arylalkyl, cycloalkyl or heteroaryl and $R^{13}$ and $R^{14}$ are independently hydrogen, phenyl, benzyl, phenethyl or 3-pyridyl. In still other embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimnethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still other embodiments, $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, aryl, arylalkyl, cycloalkyl or heteroaryl. In still other embodiments, $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, alkoxycarbonyl, substituted alkoxycarbonyl, carbamoyl or substituted carbamoyl, (preferably, when $R^{13}$ is alkoxycarbonyl, substituted alkoxycarbonyl, carbamoyl or substituted carbamoyl then $R^{14}$ is methyl, more preferably, $R^{13}$ is methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl or cyclohexyloxycarbonyl, and $R^{14}$ is methyl). In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still other embodiments, $R^{25}$ is acyl, substituted acyl, alkyl, substituted alkyl, aryl, arylalkyl, cycloalkyl or heteroaryl and $R^{13}$ and $R^{14}$ together with the atom to which they are attached form a cycloalkyl, substituted cycloalkyl, cycloheteroalkyl or substituted cycloheteroalkyl ring. In still other embodiments, $R^{25}$ is acyl, substituted acyl, alkyl, substituted alkyl, aryl, arylalkyl, cycloalkyl or heteroaryl and $R^{13}$ and $R^{14}$ together with the atom to which they are attached form a cycloalkyl or substituted cycloalkyl ring. In still other embodiments, $R^{25}$ is acyl, substituted acyl, alkyl, substituted alkyl, aryl, arylalkyl, cycloalkyl or heteroaryl, and $R^{13}$ and $R^{14}$ together with the atom to which they are attached form a cyclobutyl, cyclopentyl or cyclohexyl ring. In still other embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3- dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still other embodiments of compounds of Formula (I), $R^4$ and $R^5$ together with the carbon atom to which they are attached form a cyclobutyl or substituted cyclobutyl ring. In still other embodiments, the substituted cyclobutyl ring is substituted with one or more substituents selected from the group consisting of alkanyl, substituted alkanyl, halo, hydroxy, carboxy and alkoxycarbonyl.

In still other embodiments of compounds of Formula (I), $R^4$ and $R^5$ together with the carbon atom to which they are attached form a cyclopentyl or substituted cyclopentyl ring In still other embodiments, the cyclopentyl ring is substituted with alkanyl, substituted alkanyl, halo, hydroxy, carboxy or alkoxycarbonyl. In still other embodiments, the cyclopentyl ring is substituted with alkanyl. In still other embodiments, the cyclopentyl ring is selected from the group consisting of

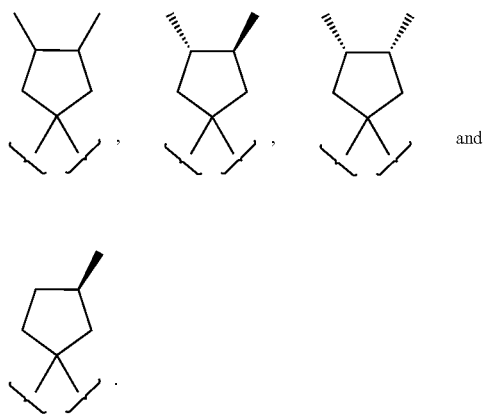

In a more specific version of the above embodiments, $R^7$ is hydrogen.

In still other embodiments of compounds of Formula (I), $R^4$ and $R^5$ together with the carbon atom to which they are attached form a cyclohexyl or substituted cyclohexyl ring. In still other embodiments, the cyclohexyl ring is substituted with alkanyl, substituted alkanyl, halo, hydroxy, carboxy or alkoxycarbonyl. In still other embodiments, the cyclohexyl ring is substituted with alkanyl. In still other embodiments, the cyclohexyl ring is selected from the group consisting of

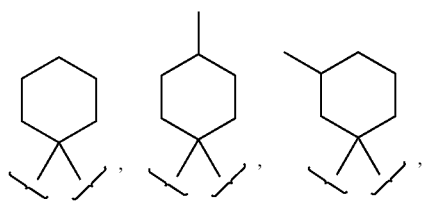

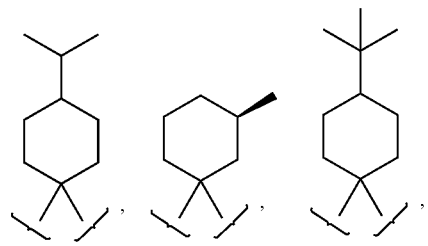

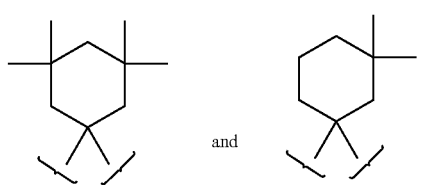

and

In a more specific version of the above embodiments, $R^7$ is hydrogen.

In still other embodiments of compounds of Formula (I), $R^4$ and $R^5$ together with the carbon atom to which they are attached form a cycloheteroalkyl or substituted cycloheteroalkyl ring. In some embodiments, n is 0. In other embodiments, n is 1, and $R^2$ is hydrogen, methyl, 2-propyl, 2-butyl, isobutyl, t-butyl, cyclopentyl, cyclohexyl, phenyl, benzyl, 4-hydroxybenzyl, 4-imidazolylmethyl, 3-indolylmethyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In still other embodiments, n is 1 and $R^2$ and $R^{16}$ together with the atoms to which they are attached form a pyrrolidine ring. Preferably, $R^4$ and $R^5$ together with the carbon atom to which they are attached form a cycloheteroalkanyl ring. More preferably, the cycloheteroalkanyl ring is selected from the group consisting of

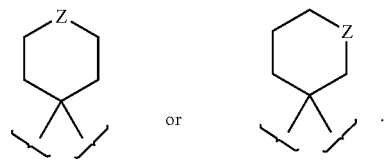

or wherein Z is O, S(O)$_p$ or NR$^{18}$;

p is 0, 1 or 2; and $R^{18}$ is selected from the group consisting of hydrogen, alkyl, substituted alkyl, acyl and alkoxycarbonyl. More preferably, the cycloheteroalkanyl ring is selected from the group consisting of

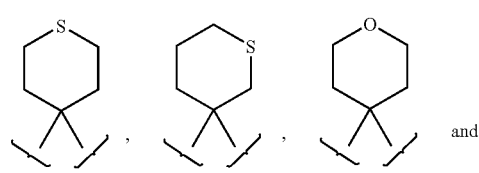

and

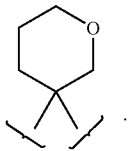

In a more specific version of the above embodiments, $R^7$ is hydrogen.

In still other embodiments of compounds of Formula (I), $R^4$ and $R^5$ together with the carbon atom to which they are attached form a bridged cycloalkyl ring. In some embodiments, n is 0. In other embodiments, n is 1 and $R^2$ is hydrogen, methyl, 2-propyl, 2-butyl, isobutyl, t-butyl, cyclopentyl, cyclohexyl, phenyl, benzyl, 4-hydroxybenzyl, 4-imidazolylmethyl, 3-indolylmethyl, —CH$_2$OH, —CH(OH)CH$_3$, —CH$_2$CO$_2$H, —CH$_2$CH$_2$CO$_2$H, —H$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In other embodiments, n is 1 and $R^2$ and $R^{16}$ together with the atoms to which they are attached form a pyrrolidine ring. Preferably, the bridged cycloalkyl group is

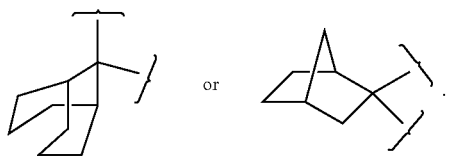

In a more specific version of the above embodiments, $R^7$ is hydrogen.

In still other embodiments of compounds of Formula (I), Y is O, $R^6$ and $R^7$ are hydrogen, $R^4$ is alkyl or cycloalkyl, $R^5$ is hydrogen or alkyl and $R^3$ is hydrogen or alkyl. In some embodiments, n is 0. In other embodiments, n is 1 and $R^2$ is hydrogen, methyl, 2-propyl, 2-butyl, isobutyl, t-butyl, cyclopentyl, cyclohexyl, phenyl, benzyl, 4-hydroxybenzyl, 4-imidazolylmethyl, 3-indolylmethyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In still other embodiments, n is 1 and $R^2$ and $R^{16}$ together with the atoms to which they are attached form a pyrrolidine ring. Preferably, $R^4$ is cycloalkyl, $R^5$ is hydrogen or methyl, and $R^3$ is hydrogen or methyl. Preferably, $R^3$ is hydrogen, $R^4$ is isobutyl and $R^5$ is hydrogen.

In still other embodiments of compounds of Formula (I), Y is O, $R^5$ and $R^7$ are hydrogen or alkanyl, $R^3$ and $R^6$ are hydrogen and $R^4$ is substituted heteroalkyl. Preferably, $R^4$ is

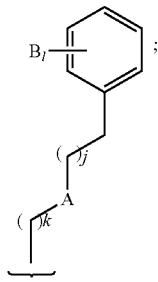

A is NR$^{19}$, O or S;
B is alkyl, substituted alkyl, alkoxy, halogen, hydroxy, carboxy, alkoxycarbonyl or amino;
$R^{19}$ is hydrogen, alkyl, cycloalkyl or aryl;
j is an integer from 0 to 4;
k is an integer from 1 to 4; and
l is an integer from 0 to 3.
More preferably, k is 1.

In still other embodiments of compounds of Formula (I), Y is O, $R^5$ and $R^7$ are hydrogen or alkanyl, $R^3$ and $R^6$ are hydrogen and $R^4$ is substituted alkanyl, cycloalkanyl or substituted cycloalkanyl. Preferably, $R^4$ is selected from the group consisting of

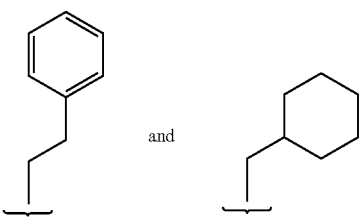

Preferably, $R^4$ is

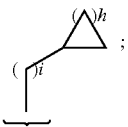

h is an integer from 1 to 6; and
i is an integer from 0 to 6.

More preferably, h is 1, 2, 3 or 4 and i is 0 or 1. Even more preferably, $R^4$ is selected from the group consisting of

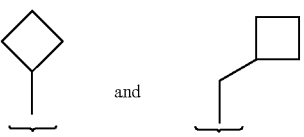

Preferably, compounds of Formula (I) are derived from a GABA analog of Formula (IV):

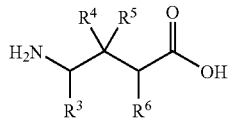

(IV)

wherein the GABA analog of Formula (IV) is selected from the group consisting of:
1-Aminomethyl-1-cyclohexane acetic acid (i.e., gabapentin);
1-Aminomethyl-1-(3-methylcyclohexane)acetic acid;
1-Aminomethyl-1-(4-methylcyclohexane)acetic acid;
1-Aminomethyl-1-(4-isopropylcyclohexane)acetic acid;
1-Aminomethyl-1-(4-tert-butylcyclohexane)acetic acid;
1-Aminomethyl-1-(3,3-dimethylcyclohexane)acetic acid;

1-Aminomethyl-1-(3,3,5,5-tetramethylcyclohexane)acetic acid;
1-Aminomethyl-1-cyclopentane acetic acid;
1-Aminomethyl-1-(3-methylcyclopentane)acetic acid;
1-Aminomethyl-1-(3,4-dimethylcyclopentane)acetic acid;
7-Aminomethyl-bicyclo[2.2.1]hept-7-yl acetic acid;
9-Aminomethyl-bicyclo[3.3.1]non-9-yl acetic acid;
4-Aminomethyl-4-(tetrahydropyran-4-yl)acetic acid;
3-Aminomethyl-3-(tetrahydropyran-3-yl)acetic acid;
4-Aminomethyl-4-(tetrahydrothiopyran-4-yl)acetic acid;
3-Aminomethyl-3-(tetrahydrothiopyran-3-yl)acetic acid;
(S)-3-Aminomethyl-5-methyl-hexanoic acid (i.e., pregabalin);
3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-cyclopropyl-hexanoic acid;
3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-phenyl-hexanoic acid;
3-Aminomethyl-5-phenyl-pentanoic acid;
3-Aminomethyl-4-cyclobutyl-butyric acid;
3-Aminomethyl-4-cyclopentyl-butyric acid;
3-Aminomethyl-4-cyclohexyl-butyric acid;
3-Aminomethyl-4-phenoxy-butyric acid;
3-Aminomethyl-5-phenoxy-hexanoic acid; and
3-Aminomethyl-5-benzylsulfanyl-pentanoic acid.

In still other embodiments, compounds of Formula (I) have the structure of Formulae (II) and (III):

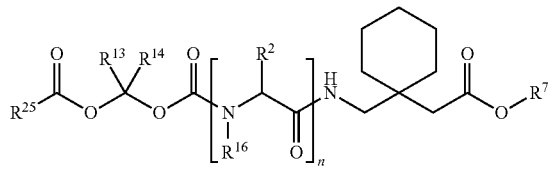

(II)

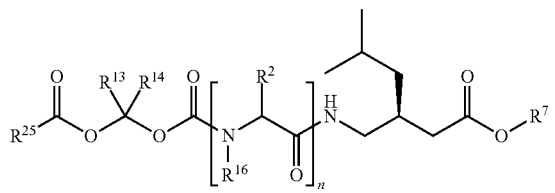

(III)

wherein n, $R^2$, $R^7$, $R^{13}$, $R^{14}$, $R^{16}$ and $R^{25}$ are as previously defined.

In some embodiments of compounds of Formulae (II) and (III), n is 0. In other embodiments, n is 1. When n is 1, preferably, the α-amino acid is of the L-stereochemical configuration.

In still other embodiments of compounds of Formulae (II) and (III), n is 1, $R^{16}$ is hydrogen and $R^2$ is hydrogen, methyl, 2-propyl, 2-butyl, isobutyl, tert-butyl, cyclopentyl, cyclohexyl, phenyl, benzyl, 4-hydroxybenzyl, 4-imidazolylmethyl, 3-indolylmethyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$ or —$CH_2CH_2CH_2NHC(NH)NH_2$. In still other embodiments, $R^{16}$ is hydrogen and $R^2$ is hydrogen, methyl, 2-propyl, 2-butyl, isobutyl, tert-butyl, cyclohexyl, phenyl or benzyl. In still other embodiments, n is 1 and $R^2$ and $R^{16}$ together with the atoms to which they are attached form a pyrrolidine ring.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1l-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is hydrogen and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is methyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is ethyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is propyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolin-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isopropyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is butyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isobutyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is sec-butyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is tert-butyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is cyclopentyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is cyclohexyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is methyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is methoxycarbonyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is ethoxycarbonyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is propoxycarbonyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isopropoxycarbonyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is butoxycarbonyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isobutoxycarbonyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is sec-butoxycarbonyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is tert-butoxycarbonyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is cyclohexyloxycarbonyl and $R^{14}$ is methyl.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is phenyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is benzyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is phenethyl and $R^{14}$ is hydrogen.

In still other embodiments of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is 3-pyridyl and $R^{14}$ is hydrogen.

In some of the embodiments described, supra, for $R^{13}$, $R^{14}$ and $R^{25}$ for compounds of Formulae (II) and (III), $R^7$ is hydrogen.

In still other embodiments, compounds of Formulae (II) and (III) have the structure of Formulae (V) and (VI), respectively

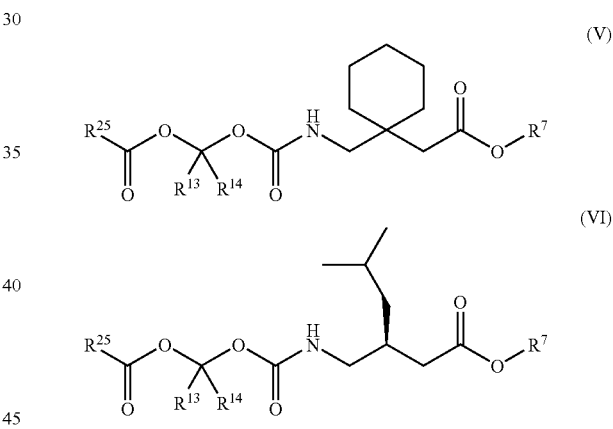

or a pharmaceutically acceptable salt, hydrate, solvate or N-oxide thereof where wherein $R^{13}$, $R^{14}$ and $R^{25}$ are as previously defined. Those of skill in the art will appreciate that the embodiments described, supra, for $R^{13}$, $R^{14}$ and $R^{25}$ for compounds of Formulae (II) and (III) are also embodiments for compounds of Formulae (V) and (VI). In some of these embodiments $R^7$ is hydrogen.

In some embodiments of compounds of Formulae (V) and (VI), $R^7$ and $R^{14}$ are each hydrogen, $R^{13}$ is $C_1$-$C_6$ alkyl and $R^{25}$ is $C_1$-$C_6$ alkyl or $C_1$-$C_6$ substituted alkyl. In some embodiments, $R^{13}$ is selected from the group consisting of methyl, ethyl, n-propyl, isopropyl, n-butyl, isobutyl and sec-butyl and $R^{25}$ is selected from the group consisting of methyl, ethyl, n-propyl, isopropyl, n-butyl, isobutyl, sec-butyl, n-pentyl, isopentyl, sec-pentyl, neopentyl and 1,1-diethoxyethyl.

In some embodiments of compounds of Formulae (V) and (VI), $R^{13}$ is methyl. In other embodiments of compound of compounds of Formulae (V) and (VI), $R^{25}$ is methyl, ethyl, n-propyl, isopropyl, n-butyl, isobutyl or sec-butyl. In still other embodiments of compounds of Formulae (V) and (VI), $R^{13}$ is methyl and $R^{25}$ is methyl, ethyl, n-propyl, isopropyl, n-butyl, isobutyl or sec-butyl. In still other embodiments of compounds of Formulae (V) and (VI), $R^{13}$ is ethyl and $R^{25}$ is methyl, ethyl, n-propyl, isopropyl, n-butyl, isobutyl or sec-butyl. In still other embodiments of compounds of Formulae (V) and (VI), $R^{13}$ is n-propyl and $R^{25}$ is methyl, ethyl, n-propyl, isopropyl, n-butyl, isobutyl or sec-butyl. In still other embodiments of compounds of Formulae (V) and (VI), $R^{13}$ is isopropyl and $R^{25}$ is methyl, ethyl, n-propyl, isopropyl, n-butyl, isobutyl or sec-butyl. In still other embodiments of compounds of Formulae (V) and (VI), $R^{13}$ is n-propyl and $R^{25}$ is n-propyl. In still other embodiments of compounds of Formulae (V) and (VI), $R^{13}$ is methyl and $R^{25}$ is ethyl. In still other embodiments of compounds of Formulae (V) and (VI), $R^{13}$ is methyl and $R^{25}$ is isopropyl. In still other embodiments of compounds of Formulae (V) and (VI), $R^{13}$ is isopropyl and $R^{25}$ is isopropyl. In still other embodiments of compounds of Formulae (V) and (VI), $R^{13}$ is isopropyl and $R^{25}$ is 1,1-diethoxyethyl. In still other embodiments of compounds of Formulae (V) and (VI), $R^{13}$ is n-propyl and $R^{25}$ is isopropyl. In still other embodiments of compounds of Formulae (V) and (VI), $R^{13}$ is n-propyl and $R^{25}$ is ethyl.

In some embodiments, the compound of Formula (V) where $R^{25}$ is isopropyl, $R^{13}$ is methyl and $R^{14}$ is hydrogen is a crystalline form of 1-{[(α-isobutanoyloxyethoxy)carbonyl]aminomethyl}-1-cyclohexane acetic acid as disclosed in Estrada et al., U.S. patent application Ser. No. 10/966,507, which claims the benefit of U.S. Provisional Application Ser. No. 60/511,287, filed Oct. 14, 2003.

Specific examples of Formula (V) compounds include 1-{[(α-acetoxyethoxy)carbonyl]aminomethyl}-1-cyclohexane acetic acid, 1-{[(α-propanoyloxyethoxy)carbonyl]aminomethyl}-1-cyclohexane acetic acid, 1-{[(α-butanoyloxyethoxy)carbonyl]aminomethyl}-1-cyclohexane acetic acid, 1-{[(α-isobutanoyloxyethoxy)carbonyl]aminomethyl}-1-cyclohexane acetic acid, 1-{[(α-pivaloxyethoxy)carbonyl]aminomethyl}-1-cyclohexane acetic acid, 1-{[(α-acetoxymethoxy)carbonyl]aminomethyl}-1-cyclohexane acetic acid, 1-{[(α-propanoyloxymethoxy)carbonyl]aminomethyl}-1-cyclohexane acetic acid, 1-{[(α-butanoyloxymethoxy)carbonyl]aminomethyl}-1-cyclohexane acetic acid, 1-{[(α-isobutanoyloxymethoxy)carbonyl]aminomethyl}-1-cyclohexane acetic acid, 1-{[(α-pivaloxymethoxy)carbonyl]aminomethyl}-1-cyclohexane acetic acid, 1-{[(α-acetoxypropoxy)carbonyl]aminomethyl}-1-cyclohexane acetic acid, 1-{[(α-propanoyloxypropoxy)carbonyl]aminomethyl}-1-cyclohexane acetic acid, 1-{[(α-butanoyloxypropoxy)carbonyl]aminomethyl}-1-cyclohexane acetic acid, 1-{[(α-isobutanoyloxypropoxy)carbonyl]aminomethyl}-1-cyclohexane acetic acid, 1-{[(α-pivaloxypropoxy)carbonyl]aminomethyl}-1-cyclohexane acetic acid, 1-{[(α-acetoxyisopropoxy)carbonyl]aminomethyl}-1-cyclohexane acetic acid, 1-{[(α-propanoyloxyisopropoxy)carbonyl]aminomethyl}-1-cyclohexane acetic acid, 1-{[(α-butanoyloxyisopropoxy)carbonyl]aminomethyl}-1-cyclohexane acetic acid, 1-{[(α-isobutanoyloxyisopropoxy)carbonyl]aminomethyl}-1-cyclohexane acetic acid, 1-{[(α-pivaloxyisopropoxy)carbonyl]aminomethyl}-1-cyclohexane acetic acid, 1-{[(α-acetoxybutoxy)carbonyl]aminomethyl}-1-cyclohexane acetic acid, 1-{[(α-propanoyloxybutoxy)carbonyl]aminomethyl}-1-cyclohexane acetic acid 1-{[(α-butanoyloxybutoxy)carbonyl]aminomethyl}-1-cyclohexane acetic acid 1-{[(α-isobutanoyloxybutoxy)carbonyl]aminomethyl}-1-cyclohexane acetic acid and 1-{[(α-pivaloxybutoxy)carbonyl]aminomethyl}-1-cyclohexane acetic acid.

Specific examples of Formula (VI) compounds include 3-{[(α-acetoxyethoxy)carbonyl]aminomethyl}-5-methyl hexanoic acid, 3-{[(α-propanoyloxyethoxy)carbonyl]aminomethyl}-5-methyl hexanoic acid, 3-{[(α-butanoyloxyethoxy)carbonyl]aminomethyl}-5-methyl hexanoic acid, 3-{[(α-isobutanoyloxyethoxy)carbonyl]aminomethyl}-5-methyl hexanoic acid, 3-{[(α-pivaloxyethoxy)carbonyl]aminomethyl}-5-methyl hexanoic acid, 3-{[(α-acetoxymethoxy)carbonyl]aminomethyl}-5-methyl hexanoic acid, 3-{[(α-propanoyloxymethoxy)carbonyl]aminomethyl}-5-methyl hexanoic acid, 3-{[(α-butanoyloxymethoxy)carbonyl]aminomethyl}-5-methyl hexanoic acid, 3-{[(α-isobutanoyloxymethoxy)carbonyl]aminomethyl}-5-methyl hexanoic acid, 3-{[(α-pivaloxymethoxy)carbonyl]aminomethyl}-5-methyl hexanoic acid, 3-{[(α-acetoxypropoxy)carbonyl]aminomethyl}-5-methyl hexanoic acid, 3-{[(α-propanoyloxypropoxy)carbonyl]aminomethyl}-5-methyl hexanoic acid, 3-{[(α-butanoyloxypropoxy)carbonyl]aminomethyl}-5-methyl hexanoic acid, 3-{[(α-isobutanoyloxypropoxy)carbonyl]aminomethyl}-5-methyl hexanoic acid, 3-{[(α-pivaloxypropoxy)carbonyl]aminomethyl}-5-methyl hexanoic acid, 3-{[(α-acetoxyisopropoxy)carbonyl]aminomethyl}-5-methyl hexanoic acid, 3-{[(α-propanoyloxyisopropoxy)carbonyl]aminomethyl}-5-methyl hexanoic acid, 3-{[(α-butanoyloxyisopropoxy)carbonyl]aminomethyl}-5-methyl hexanoic acid, 3-{[(α-isobutanoyloxyisopropoxy)carbonyl]aminomethyl}-5-methyl hexanoic acid, 3-{[(α-pivaloxyisopropoxy)carbonyl]aminomethyl}-5-methyl hexanoic acid, 3-{[(α-acetoxybutoxy)carbonyl]aminomethyl}-5-methyl hexanoic acid, 3-{[(α-propanoyloxybutoxy)carbonyl]aminomethyl}-5-methyl hexanoic acid, 3-{[(α-butanoyloxybutoxy)carbonyl]aminomethyl}-5-methyl hexanoic acid, 3-{[(α-isobutanoyloxybutoxy)carbonyl]aminomethyl}-5-methyl hexanoic acid and 3-{[(α-pivaloxybutoxy)carbonyl]aminomethyl}-5-methyl hexanoic acid.

4.3 Methods of Synthesis of Prodruis of GABA Analogs

Methods of synthesis of prodrugs of GABA analogs, including methods of synthesizing compounds of structural Formulae (I), (II), (III), (V) and (VI) are disclosed in Gallop et al., International Publication No. WO 02/100347, Gallop et al., International Publication No. WO03/077902, Raillard et al., International Publication No. WO03/104184 and Bhat et al., U.S. patent application Ser. No. 10/893,130, filed Jul. 15, 2004. Other methods for synthesis of prodrugs of GABA analogs have also been disclosed (see Bryans et al., International Publication No. WO 01/90052; U.K. Application GB 2,362,646; European Applications EP 1,201,240 and 1,178, 034; Yatvin et al., U.S. Pat. No. 6,024,977; Gallop et al., International Publication No. WO 02/28881; Gallop et al., International Publication No. WO 02/28883; Gallop et al., International Publication No. WO 02/28411; Gallop et al., International Publication No. WO 02/32376; Gallop et al., International Publication No. WO 02/42414).

4.4 Therapeutic Methods of Use

In some embodiments, a prodrug of a GABA analog and/or pharmaceutical composition thereof is administered to a patient suffering from RLS. In other embodiments, a prodrug of a GABA analog and/or pharmaceutical composition thereof is administered to a patient as a preventative measure against RLS. The suitability of GABA analog prodrugs and/or pharmaceutical compositions thereof to treat or prevent RLS may be readily determined by methods known to the skilled artisan. The present methods encompass either reducing the number and/or frequency of RLS episodes or reducing the severity of restless legs syndrome or both.

The patient is a mammal, preferably a human. The patient may be female or male of any age. Preferably, the patient is an adult, more preferably, the patient is over 65 years of age. Patients with idiopathic RLS benefit from the methods disclosed herein.

In addition, patients with certain medical conditions (e.g., dialysis, end stage renal disease, hypothyroidism, diabetes, decreased magnesium levels and folate levels) may particularly benefit from the methods disclosed herein. In some embodiments, a prodrug of a GABA analog and/or pharmaceutical compositions thereof is administered to a iron deficient patient suffering from RLS. In other embodiments, a prodrug of a GABA analog and/or pharmaceutical compositions thereof is administered to a dialysis patient suffering from RLS.

While sentient, inactive RLS patients, (e.g., who are sitting or lying down), experience an intensely uncomfortable sensation in their legs and occasionally in other extremities that compels movement. Patients treated according to the methods disclosed herein may find a reduction in the frequency of such sensations, a decreased intensity of each episode or complete cessation of such episodes.

Many patients with RLS also experience periodic leg movements during sleep (PLMS). PLMS typically occurs in clusters throughout the night, with a periodicity of 20 to 40 seconds. Patients can be aroused and find that the sleep interruption is sufficient to cause daytime drowsiness. In addition, RLS patients with PLMS report insomnia and when asleep, find that sleep is not restorative and of poor quality. When treated in accordance with the methods disclosed herein, RLS patients with PLMS may find that the frequency of incidents of disruptive leg movements diminishes or complete cessation of the episodes. Subjectively, RLS patients with PLMS treated by the methods disclosed herein may find decreased insomnia and improved sleep quality. Formal sleep studies (see below) may show a significantly reduced periodic leg movements during sleep (PLMS) index and improved sleep architecture.

In some embodiments, administering a GABA analog prodrug or pharmaceutical composition thereof to a patient suffering from RLS improves the sleep of the patient. Improvement of sleep can be measured both quantitatively and qualitatively. For example, qualitatively, sleep improvement can be determined by any number of factors including, but not limited to, an easier time falling asleep, a decrease in the frequency of waking up in the middle of the night, waking up at an appropriate time (i.e., not too early in the morning) and getting good quality sleep that enables the individual to feel refreshed the following day. Factors which can be used to determine improvement in sleep quantitatively include, but are not limited to, polysomnographic data demonstrating increased sleep efficiency, more time spent asleep in deeper stages of sleep such as Stage 2-4 as opposed to Stage 1 and decreased number of periodic limb movements. Preferably, total sleep architecture (increased total sleep time, sleep efficiency, and slow wave sleep, and decreased stage 1 sleep) is improved. Standardized methods of determining the extent of symptom reduction in RLS patients and in RLS patients with PLMS, include assessment by means of the International RLS Study Group Rating Scale, the Pittsburg Sleep Quality Index and the Clinical Global Impression of Change.

The compounds disclosed herein, particularly the gabapentin prodrug 1-{[(α-isobutanoyloxyethoxy)carbonyl]aminomethyl}-1-cyclohexane acetic acid, may be more efficacious than the parent drug molecule (e.g., gabapentin or other GABA analog) in treating or preventing RLS because the disclosed compounds require less time to reach a therapeutic concentration in the blood, i.e., the compounds disclosed herein have a shorter $T_{max}$ than their parent drug counterparts when taken orally as an immediate release dosage form. Without wishing to bound by theory, it is believed that the compounds disclosed herein, particularly the gabapentin prodrug 1-{[(α-isobutanoyloxyethoxy)carbonyl]aminomethyl}-1-cyclohexane acetic acid, are absorbed from the gastrointestinal lumen into the blood by a different mechanism than that by which gabapentin and other known GABA analogs are absorbed. For example, gabapentin is believed to be actively transported across the gut wall by a carrier transporter localized in the human small intestine. The gabapentin transporter is easily saturated which means that the amount of gabapentin absorbed into the blood may not be proportional to the amount of gabapentin that is administered orally, since once the transporter is saturated, further absorption of gabapentin does not occur to any significant degree. In comparison to gabapentin, the compounds disclosed herein, particularly, the gabapentin prodrug 1-{[(α-isobutanoyloxyethoxy)carbonyl]aminomethyl}-1-cyclohexane acetic acid, are absorbed across the gut wall along a greater portion of the gastrointestinal tract, including the colon.

Because the compounds disclosed herein can be formulated in sustained release formulations which provide for sustained release over a period of hours into the gastrointestinal tract and particularly, release within the colon, the compounds (especially, the gabapentin prodrug 1-{[(α-isobutanoyloxyethoxy)carbonyl]aminomethyl}-1-cyclohexane acetic acid) may also be more efficacious than their respective parent drugs (e.g., gabapentin or other GABA analog) in treating or preventing RLS. The ability of the compounds disclosed herein to be used in sustained release oral dosage forms reduces the dosing frequency necessary for maintenance of a therapeutically effective drug concentration in the blood. Importantly, administration in the evening of the GABA analog prodrug from a sustained release oral dosage form can provide for therapeutic concentrations of the GABA analog throughout the night, thereby enabling more effective relief of a patient's RLS symptoms than can be achieved by direct administration of the GABA analog itself.

4.5 Therapeutic/Prophylactic Administration

Dosage forms comprising prodrugs of GABA analogs may be advantageously used to treat or prevent RLS. The dosage forms may be administered or applied singly, or in combination with other agents. The dosage forms may also deliver a prodrug of a GABA analog to a patient in combination with another pharmaceutically active agent, including another prodrug of a GABA analog. The patient is a mammal and more preferably, a human.

When used in the present methods of treatment, the dosage forms upon releasing a prodrug of a GABA analog in vivo preferably, provide the GABA analog (e.g., gabapentin or pregabalin) in the systemic circulation of the patient. While not wishing to bound by theory, the promoiety or promoieties of the prodrug may be cleaved either chemically and/or enzymatically. One or more enzymes present in the stomach, intestinal lumen, intestinal tissue, blood, liver, brain or any other suitable tissue of a mammal may cleave the promoiety or promoieties of the prodrug. The mechanism of cleavage is not important to the current methods. Preferably, the GABA analog that is formed by cleavage of the promoiety from the prodrug does not contain substantial quantities of lactam contaminant (preferably, less than about 0.5% by weight, more preferably, less than about 0.2% by weight, most preferably, less than about 0.1% by weight) for the reasons described in Augart et al., U.S. Pat. No. 6,054,482. The extent of release of lactam contaminant from the prodrugs may be assessed using standard in vitro analytical methods.

Some therapeutically effective GABA analogs, e.g., gabapentin and pregabalin, have poor passive permeability across the gastrointestinal mucosa, probably because of their zwitterionic character at physiological pH. Gabapentin, pregabalin and other GABA analogs are actively transported across the gastrointestinal tract by one or more amino acid transporters (e.g., the "large neutral amino acid transporter"). However, the large neutral amino acid transporter is expressed predominantly within cells lining the lumen of a limited region of the small intestine, which provides limited window for drug absorption and leads to an overall dose-dependent drug bioavailability that decreases with increasing dose.

A class of GABA analog prodrugs are those suitable for oral administration. The promoiety or promoieties are preferably cleaved after absorption by the gastrointestinal tract (e.g., in intestinal tissue, blood, liver or other suitable tissue of the patient) with orally administered GABA analog prodrugs. The promoiety or promoieties may make the prodrug a substrate for one or more transporters expressed in the large intestine (i.e., colon), and/or may let the prodrug be passively absorbed across the mucosa for GABA analogs that are poorly absorbed across the gastrointestinal mucosa (e.g., gabapentin and pregabalin).

4.6 Pharmaceutical Compositions

The pharmaceutical compositions disclosed herein comprise a therapeutically effective amount of one or more GABA analog prodrugs, preferably, in purified form, together with a suitable amount of a pharmaceutically acceptable vehicle, so as to provide a form for proper administration to a patient. Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds disclosed herein into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). Preferred pharmaceutical compositions are formulated for oral delivery, particularly for oral sustained release administration.

Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

When a GABA analog prodrug is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

The pharmaceutical compositions preferably contain no or only low levels of lactam side products formed by intramolecular cyclization of the GABA analog and/or GABA analog prodrug. In a preferred embodiment, the compositions are stable to extended storage (preferably, greater than one year) without substantial lactam formation (preferably, less than about 0.5% lactam by weight, more preferably, less than about 0.2% lactam by weight, most preferably, less than about 0.1% lactam by weight).

4.7 Sustained Release Oral Dosage Forms

The methods that involve oral administration of a GABA analog prodrug to treat or prevent RLS can be practiced with a number of different dosage forms, which provide sustained release of the prodrug. Such sustained release oral dosage forms are particularly preferred for administering those GABA analog prodrugs that are absorbed by cells lining the large intestine, since these dosage forms are generally well adapted to deliver a prodrug to that location of the gastrointestinal tract.

In some embodiments, the dosage form is comprised of beads that on dissolution or diffusion release the prodrug over an extended period of hours, preferably, over a period of at least 6 hours, more preferably, over a period of at least 8 hours and most preferably, over a period of at least 12 hours. The prodrug-releasing beads may have a central composition or core comprising a prodrug and pharmaceutically acceptable vehicles, including optional lubricants, antioxidants and buffers. The beads may be medical preparations with a diameter of about 1 to about 2 mm. Individual beads may comprise doses of the prodrug, for example, doses of up to about 40 mg of prodrug. The beads, in some embodiments, are formed of non-cross-linked materials to enhance their discharge from the gastrointestinal tract. The beads may be coated with a release rate-controlling polymer that gives a timed release profile.

The time release beads may be manufactured into a tablet for therapeutically effective prodrug administration. The beads can be made into matrix tablets by direct compression of a plurality of beads coated with, for example, an acrylic resin and blended with excipients such as hydroxypropylmethyl cellulose. The manufacture of beads has been disclosed in the art (Lu, *Int. J. Pharm.* 1994, 112, 117-124; Pharmaceutical Sciences by Remington, 14$^{th}$ ed, pp 1626-1628 (1970); Fincher, *J. Pharm. Sci.* 1968, 57, 1825-1835; Benedikt, U.S. Pat. No. 4,083,949) as has the manufacture of tablets (Pharmaceutical Sciences, by Remington, 17$^{th}$ Ed, Ch. 90, pp 1603-1625 (1985).

In other embodiments, an oral sustained release pump may be used (Langer, supra; Sefton, 1987, *CRC Crit Ref Biomed. Eng.* 14:201; Saudek et al., 1989, *N. Engl. J Med.* 321:574).

In other embodiments, polymeric materials can be used (See "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, N.Y. (1984); Langer et al., 1983, *J Macromol. Sci. Rev. Macromol Chem.* 23:61; Levy et al., 1985, *Science* 228: 190; During et al., 1989, *Ann. Neurol.* 25:351; Howard et al., 1989, *J. Neurosurg.* 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described (Alderman, *Int. J. Pharm. Tech. & Prod. Mfr.* 1984, 5(3) 1-9). Factors affecting drug release are well known to the skilled artisan and have been described in the art (Bamba et al., *Int. J. Pharm.* 1979, 2, 307).

In other embodiments, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In yet other embodiments, drug-releasing lipid matrices can be used for oral sustained release administration. One particularly preferred example is when solid microparticles of the prodrug are coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In yet other embodiments, prodrug-releasing waxes can be used for oral sustained release administration. Examples of suitable sustained prodrug-releasing waxes are disclosed in Cain et al., U.S. Pat. No. 3,402,240 (carnauba wax, candedilla wax, esparto wax and ouricury wax); Shtohryn et al., U.S. Pat. No. 4,820,523 (hydrogenated vegetable oil, bees wax, caranuba wax, paraffin, candelillia, ozokerite and mixtures thereof); and Walters, U.S. Pat. No. 4,421,736 (mixture of paraffin and castor wax).

In still other embodiments, osmotic delivery systems are used for oral sustained release administration (Verma et al., *Drug Dev. Ind. Pharm.* 2000, 26:695-708). In a preferred embodiment, OROS® systems made by Alza Corporation, Mountain View, Calif. are used for oral sustained release delivery devices (Theeuwes et al., U.S. Pat. No. 3,845,770; Theeuwes et al., U.S. Pat. No. 3,916,899).

In yet other embodiments, a controlled-release system can be placed in proximity of the target of the prodrug of the GABA analog GABA analog, thus requiring only a fraction of the systemic dose (See, e.g., Goodson, in "Medical Applications of Controlled Release," supra, vol. 2, pp. 115-138 (1984)). Other controlled-release systems are discussed in Langer, 1990, *Science* 249:1527-1533 may also be used.

In other embodiments, the dosage form comprises a prodrug of a GABA analog coated on a polymer substrate. The polymer can be an erodible, or a nonerodible polymer. The coated substrate may be folded onto itself to provide a bilayer polymer drug dosage form. For example, a prodrug of a GABA analog can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the prodrug over a sustained release period. Representative biodegradable polymers comprise a member selected from the group consisting of biodegradable poly(amides), poly(amino acids), poly(esters), poly (lactic acid), poly(glycolic acid), poly(carbohydrate), poly (orthoester), poly(orthocarbonate), poly(acetyl), poly (anhydrides), biodegradable poly(dihydropyrans), and poly (dioxinones) which are known in the art (Rosoff, *Controlled Release of Drugs*, Chap. 2, pp. 53-95 (1989); Heller et al., U.S. Pat. No. 3,811,444; Michaels, U.S. Pat. No. 3,962,414; Capozza, U.S. Pat. No. 4,066,747; Schmitt, U.S. Pat. No. 4,070,347; Choi et al., U.S. Pat. No. 4,079,038; Choi et al., U.S. Pat. No. 4,093,709).

In other embodiments, the dosage form comprises a prodrug loaded into a polymer that releases the prodrug by diffusion through a polymer, or by flux through pores or by rupture of a polymer matrix. The drug delivery polymeric dosage form comprises a concentration of 10 mg to 2500 mg homogenously contained in or on a polymer. The dosage form comprises at least one exposed surface at the beginning of dose delivery. The non-exposed surface, when present, is coated with a pharmaceutically acceptable material impermeable to the passage of a prodrug. The dosage form may be manufactured by procedures known in the art. An example of providing a dosage form comprises blending a pharmaceutically acceptable carrier like polyethylene glycol, with a known dose of prodrug at an elevated temperature, (e.g., 37° C.), and adding it to a silastic medical grade elastomer with a cross-linking agent, for example, octanoate, followed by casting in a mold. The step is repeated for each optional successive layer. The system is allowed to set for about 1 hour, to provide the dosage form. Representative polymers for manufacturing the dosage form comprise a member selected from the group consisting of olefin, and vinyl polymers, addition polymers, condensation polymers, carbohydrate polymers, and silicone polymers as represented by polyethylene, polypropylene, polyvinyl acetate, polymethylacrylate, polyisobutylmethacrylate, polyalginate, polyamide and polysilicone. The polymers and procedures for manufacturing them have been described in the art (Coleman et al., *Polymers* 1990, 31,1187-1231; Roerdink et al., *Drug Carrier Systems* 1989, 9, 57-10; Leong et al., *Adv. Drug Delivery Rev.* 1987, 1, 199-233; Roff et al., *Handbook of Common Polymers* 1971, CRC Press; Chien et al., U.S. Pat. No. 3,992,518).

In other embodiments, the dosage from comprises a plurality of tiny pills. The tiny time-release pills provide a number of individual doses for providing various time doses for achieving a sustained-release prodrug delivery profile over an extended period of time up to 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin, and a hydrophilic colloid. The hydrophilic matrix comprises a plurality of 4 to 50 tiny pills, each tiny pill comprise a dose population of from 10 ng, 0.5 mg, 1 mg, 1.2 mg, 1.4 mg, 1.6 mg, 5.0 mg, etc. The tiny pills comprise a release rate-controlling wall of 0.001 mm up to 10 mm thickness to provide for the timed release of prodrug. Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in Urquhart et al., U.S. Pat. No. 4,434,153; Urquhart et al., U.S. Pat. No. 4,721,613; Theeuwes, U.S. Pat. No. 4,853,229; Barry, U.S. Pat. No. 2,996,431; Neville, U.S. Pat. No. 3,139,383; Mehta, U.S. Pat. No. 4,752,470.

In other embodiments, the dosage form comprises an osmotic dosage form, which comprises a semipermeable wall that surrounds a therapeutic composition comprising the prodrug. In use within a patient, the osmotic dosage form comprising a homogenous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to 24 hours (or even in some cases up to 30 hours) to provide controlled and sustained prodrug release. These delivery platforms can provide an essentially zero order delivery profile as opposed to the spiked profiles of immediate release formulations.

In other embodiments, the dosage form comprises another osmotic dosage form comprising a wall surrounding a compartment, the wall comprising a semipermeable polymeric composition permeable to the passage of fluid and substantially impermeable to the passage of prodrug present in the compartment, a prodrug-containing layer composition in the compartment, a hydrogel push layer composition in the compartment comprising an osmotic formulation for imbibing and absorbing fluid for expanding in size for pushing the prodrug composition layer from the dosage form, and at least one passageway in the wall for releasing the prodrug composition. The method delivers the prodrug by imbibing fluid through the semipermeable wall at a fluid imbibing rate determined by the permeability of the semipermeable wall and the osmotic pressure across the semipermeable wall causing the push layer to expand, thereby delivering the prodrug from the dosage form through the exit passageway to a patient over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 weight-average molecular weight which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer comprises 0.0 mg to 350 mg, in present manufacture; 0.1 mg to 250 mg of a hydroxyalkylcellulose of 7,500 to 4,500,00 weight-average molecular weight (e.g., hydroxymethylcellulose, hydroxyethylcellulose, hydroxypropylcellulose, hydroxybutylcellulose or hydroxypentylcellulose) in present manufacture; 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylated hydroxyquinone, butylhydroxyanisole, hydroxycomarin, butylated hydroxytoluene, cephalm, ethyl gallate, propyl gallate, octyl gallate, lauryl gallate, propylhydroxybenzoate, trihydroxybutylrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

In the osmotic dosage forms, the semipermeable wall comprises a composition that is permeable to the passage of fluid and impermeable to the passage of prodrug. The wall is non-toxic and comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkycellulose such as hydroxypropylmethylcellulose. The total weight percent of all components comprising the wall is equal to 100 wt %. The internal compartment comprises the prodrug-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of prodrug to a patient over time. The dosage form comprises a passageway in the wall that connects the exterior of the dosage form with the internal compartment. The osmotic powered dosage form can be made to deliver prodrug from the dosage form to the patient at a zero order rate of release over a period of up to about 24 hours.

The expression "passageway" as used herein comprises means and methods suitable for the metered release of the prodrug from the compartment of the dosage form. The exit means comprises at least one passageway, including orifice, bore, aperture, pore, porous element, hollow fiber, capillary tube, channel, porous overlay, or porous element that provides for the osmotic controlled release of prodrug. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic)acid or poly(lactic)acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of prodrug from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in Theeuwes et al., U.S. Pat. No. 3,845,770; Theeuwes et al., U.S. Pat. No. 3,916,899; Saunders et al., U.S. Pat. No. 4,063,064; Theeuwes et al., U.S. Pat. No. 4,088,864 and Ayer et al., U.S. Pat. No. 4,816,263. Passageways formed by leaching are disclosed in Ayer et al., U.S. Pat. No. 4,200,098 and Ayer et al., U.S. Pat. No. 4,285,987.

In order to decrease dosing frequency and augment the convenience to the patient and increase patient compliance, the sustained release oral dosage form (regardless of the specific form of the sustained release dosage form) preferably provides therapeutic concentrations of the GABA analog in the patient's blood over a period of at least about 6 hours, more preferably, over a period of at least about 8 hours, and most preferably, over a period of at least about 12 hours. However, certain RLS patients may only require therapeutic concentrations of the GABA analog while they are sleeping and for such patients, a sustained release oral dosage form that is taken shortly before bedtime and which provides therapeutic concentrations of the GABA analog while the patient is sleeping, e.g., for periods of about 7 to 10 hours, may be suitable. For example, the sustained release dosage form may release from 0 to 30% of the prodrug in 0 to 2 hours, from 20 to 50% of the prodrug in 2 to 12 hours, from 50 to 85% of the prodrug in 3 to 20 hours and greater than 75% of the prodrug in 5 to 18 hours. The sustained release oral dosage form may fuirther provide a concentration of the GABA analog in the blood plasma of the patient over time, which curve has an area under the curve (AUC) that is proportional to the dose of the prodrug of GABA analog administered, and a maximum concentration $C_{max}$. The $C_{max}$ may be less than 75%, and is preferably, less than 60%, of the $C_{max}$ obtained from administering an equivalent dose of the prodrug from an immediate release oral dosage form, and the AUC is preferably substantially the same as the AUC obtained from administering an equivalent dose of the prodrug from an immediate release oral dosage form.

For example, the dosage forms can be administered twice per day, or once per day.

4.8 Methods of Administration and Doses

The present methods for treatment or prevention of RLS require administration of a GABA analog prodrug, or a pharmaceutical composition thereof, to a patient in need of such treatment or prevention. The compounds and/or pharmaceutical compositions thereof are preferably administered orally. The compounds and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. Preferably, the compounds and/or pharmaceutical compositions thereof are delivered via sustained release dosage forms, more preferably via oral sustained release dosage forms.

The amount of GABA analog prodrug that will be effective in the treatment or prevention of RLS in a patient will depend on the specific nature of the condition and can be determined by standard clinical techniques known in the art. In addition, in vitro or in vivo assays may optionally be employed to help identify optimal dosage ranges. The amount of a prodrug administered will, of course, be dependent on, among other factors, the subject being treated, the weight of the subject, the severity of the affliction, the manner of administration and the judgment of the prescribing physician.

Preferably, the dosage forms are adapted to be administered to a patient no more than twice per day, more preferably, only once per day. Dosing may be provided alone or in combination with other drugs and may continue as long as required for effective treatment or prevention of RLS.

Suitable dosage ranges for oral administration are dependent on the potency of the particular GABA analog (once cleaved from the promoiety), but are generally about 0.1 mg to about 200 mg of GABA analog per kilogram body weight per day, more preferably about 1 to about 100 mg/kg-body wt. per day. Preferably, the GABA analog prodrug is a prodrug of gabapentin or pregabalin. When the GABA analog is gabapentin, typical daily doses of the gabapentin in adult patients are 300 mg/day to 3600 mg/day and the dose of gabapentin prodrug may be adjusted to provide an equivalent molar quantity of gabapentin. When the GABA analog prodrug is 1-{[(α-isobutanoyloxyethoxy)carbonyl]-aminomethyl}-1-cyclohexane acetic acid, typical doses of the prodrug can be for example 100, 200, 300, 400, 500, 600, 700, 800, 900, 1000 mg/dose, with up to 4 doses administered per day. Other GABA analogs may be more potent than gabapentin and lower doses may be appropriate for both the cleaved drug and any prodrug (measured on an equivalent molar basis). For example, typical doses for pregabalin in the range of 100 mg/day to 600 mg/day are appropriate. Dosage ranges may be readily determined by methods known to the skilled artisan.

4.9 Combination Therapy

In certain embodiments, GABA analog prodrugs and/or pharmaceutical compositions thereof can be used in combination therapy with at least one other therapeutic agent which may be a different GABA analog prodrug. The GABA analog prodrug and/or pharmaceutical composition thereof and the therapeutic agent can act additively or, more preferably, synergistically. In some embodiments, a GABA analog prodrugs and/or a pharmaceutical composition thereof is administered concurrently with the administration of another therapeutic agent. For example, a GABA analog prodrug may be administered together with a dopamine agonist such as L-dopa, pergolide, pramipexole or ropinirole. In other embodiments, GABA analog prodrugs and/or pharmaceutical composition thereof is administered prior or subsequent to administration of another therapeutic agent.

5. EXAMPLES

Reference is now made to the following examples, which describe in detail, preparation of sustained release dosage form and methods for using GABA analog prodrugs to treat RLS. It will be apparent to those skilled in the art that many modifications, both to materials and methods, may be practiced without departing from the scope thereof.

5.1 Example 1

Preparation of a Sustained Release Oral Dosage Form of 1-{[(α-Isobutanoyloxyethoxy)carbonyl] aminomethyl}-1-Cyclohexane Acetic Acid A sustained release oral osmotic delivery dosage form containing the gabapentin prodrug 1-{[(α-isobutanoyloxyethoxy)carbonyl]aminomethyl}-1-cyclohexane acetic acid is prepared following methods described in Ayer et al., U.S. Pat. No. 5,707,663. Accordingly, 660 grams of 1-{[(α-isobutanoyloxyethoxy)carbonyl]aminomethyl}-1-cyclohexane acetic acid and 30 grams of pharmaceutically acceptable polyethylene oxide, (5,000,000 molecular weight) is added to the bowl of a fluid bed granulator. The microencapsulation process is computerized and atomized in cycles. The process is initiated by first fluidizing the dry drug and the polymer powder for 3 minutes and the blended granules are microencapsulated with an aqueous hydroxypropylmethylcellulose solution. The polymer solution is prepared by dissolving 35 grams of hydroxypropylmethylcellulose comprising 11,200 molecular weight in 400 grams of water. The operating conditions are as follows: spray rate of 50 grams/min/nozzle (2 nozzles are used), inlet temperature 50° C.; outlet temperature 37° C. and process air flow of 400 ft$^3$/minute. During the coating process, the filter bag is shaken for 10 seconds after every 15 seconds of solution spraying to remove any uncoated materials. A total of 270 grams of solution is applied. After solution spraying, the microencapsulated powder is dried in the granulator to reach a moisture content of 0.25%. The dried granulation is then passed through a 16 mesh screen. Next, a total of 5.3 grams of magnesium stearate is weighed out, screened through a 40 mesh screen, and blended into the granulation using a V-blender for 2 minutes. The granulation is stored in a tightly closed bag with desiccants.

The osmotic displacement-push composition is then prepared as follows: first, 3.7 kg of sodium chloride, and 150 grams of red ferric oxide are separately screened through an 8 mesh screen using a Quadro comil. Then, the screened ingredients plus 7.6 kg of pharmaceutically acceptable grade polyethylene oxide (7,500,000 molecular weight) and 250 grams of hydroxypropylmethylcellulose (11,200 molecular weight,) are dispensed into the bowl of a Glatt fluid bed granulator. Next, the dry powders are air suspended and mixed for 3 minutes. To prepare the binder solution 420 grams of hydroxypropylmethylcellulose (11,200 molecular weight) is dissolved in 4.85 kg of water and 9.4 grams of butylated hydroxytoluene is dissolved in 60 grams of denatured ethanol. The two solutions are combined and mixed to form the final binder solution. The conditions monitored during the process are as follows: solution spray rate of 400 g/min (3 nozzles are used); inlet temperature 45° C.; outlet temperature 24° C. and process air flow of 1,500 ft$^3$/minute. The granulating process is computerized and automated in cycles. Each cycle contains 1.5 minutes of solution spraying followed by 10 seconds of bag shaking to remove any possible powder deposits. A total of 4.4 kg of solution is sprayed. After solution spraying, the granulated particles are dried in the granulator for 50 minutes at 21° C. to reach a moisture content of 0.3%. The granules are removed and sized through an 8 mesh screen. Then, 28 grams of magnesium stearate, screened through a 16 mesh screen, is mixed into the granulation using a tumbler for 3 minutes at 8 rpm.

Next, the 1-{[(α-isobutanoyloxyethoxy)carbonyl]aminomethyl}-1-cyclohexane acetic acid drug composition and the push composition are compressed using a tablet press into bilayer cores of tablet shape as follows: first 700 mg of 1-{[(α-isobutanoyloxyethoxy)carbonyl]aminomethyl}-1-cyclohexane acetic acid drug composition is added to a punch and lightly precompressed, then 421 mg of the push composition is added and the layers are pressed under a pressure head of 1.5 ton (3000 lbs) into a 0.75" length modified capsule contacting layered arrangement. The compression process is done in a humidity controlled environment. The relative humidity during the process is 35% RH (relative humidity) or lower. The compressed cores are stored in a tightly closed bag with desiccants.

The bilayered arrangements next are coated with a semipermeable wall. The wall-forming composition comprises 100% cellulose acetate having a ~40% acetyl content. The polymer is dissolved in 100% acetone to make a 4% solid solution. The wall forming composition is sprayed at 26 grams/min onto and around the bilayer cores in a tablet coater until a dry weight of 90 mg/core is achieved. Next, one 10 mil (0.254 mm) exit passageway is mechanically drilled through the semipermeable wall to connect the drug layer with the exterior of the dosage system. The residual solvent is removed by first drying for 120 hours at 50° C. and 30% relative humidity, then the systems are dried for 2 hours at 50° C. to remove excess moisture. The drug dosage form produced by this process provides: ~90 wt % 1-{[(α-isobutanoyloxyethoxy)carbonyl]aminomethyl}-1-cyclohexane acetic acid, 4 wt % hydroxypropylmethylcellulose of 11,200 molecular weight, 4 wt % polyethylene oxide of 5,000,000 molecular weight and 1 wt % magnesium stearate in the drug layer. The push composition comprises 63.7 wt % polyethylene oxide of 7,500,000 molecular weight, 30 wt % sodium chloride, 5 wt % hydroxypropylmethylcellulose of 11,200 molecular weight, 1 wt % red ferric oxide, 0.25 wt % magnesium stearate, and 0.075 wt % of butylated hydroxytoluene. The wall comprises 100 wt % cellulose acetate comprising a ~40% acetyl content. The dosage form has one passageway, 10 mils (0.254 mm), and it has a 1-{[(α-isobutanoyloxyethoxy)carbonyl]aminomethyl}-1-cyclohexane acetic acid release rate of >20 mg/hr and a half life for drug release of >8 hours in artificial gastric fluid.

5.2 Example 2

Administration of 1-{[(α-Isobutanoyloxyethoxy) carbonyl]-aminomethyl}-1-Cyclohexane Acetic Acid for The Treatment of Restless Legs Syndrome A placebo-controlled, cross-over clinical trial is conducted to assess the effects of the prodrug 1-{[(α-isobutanoyloxyethoxy)carbonyl]-aminomethyl}-1-cyclohexane acetic acid on sensory and motor symptoms in patients with restless legs syndrome (Garcia-Borreguero et al., *Neurology* 2002 (11:2) 1573-79). Briefly, twenty patients with RLS (either idiopathic or secondary) are randomized and treated for 6 weeks with either the prodrug or placebo. The prodrug is formulated as osmotic sustained release capsules containing 700 mg prodrug (preparation of the sustained release capsules is described in Section 5.1 above) and is administered two capsules twice daily (2800 mg/day, equal to ~1400 mg gabapentin equivalents/day). After a 1-week washout, the patients are crossed over to alternative treatment for 6 weeks. Patients are rated at baseline and at scheduled intervals by the RLS Rating Scale, Clinical Global Impression, pain analog scale, and Pittsburgh Sleep Quality Index. In addition, all-night polysomnography is performed before and after the drug treatment periods (Foldvary-Schaefer et al., *Epilepsia* 2002 (43: 12) 1493-1497). A positive result for the prodrug is associated with reduced symptoms on all rating scales when compared with the placebo.

5.3 Example 3

Administration of 1-{[(α-Isobutanoyloxyethoxy) carbonyl]-aminomethyl}-1-Cyclohexane Acetic Acid for The Treatment of Restless Legs Syndrome A randomized, double-blind, placebo-controlled, crossover study comparing the gabapentin prodrug, 1-{[(α-isobutanoyloxyethoxy)carbonyl]-aminomethyl}-1-cyclohexane acetic acid, with placebo in approximately 40 human patients with restless legs syndrome (RLS) has been started to assess the safety of the prodrug and the efficacy of the prodrug for reducing symptoms of RLS and for improving the quality of sleep. As of the filing date hereof, the study was ongoing and the results of the study are not yet available. The patients were selected based upon (1) a diagnosis of RLS using the International RLS Study Group Diagnostic Criteria, (2) having had no previous medical treatment for their RLS, and (3) exhibiting RLS symptoms for a minimum of 15 nights during the previous month. Eligible patients were randomized to take either prodrug or placebo for 14 days of treatment, then undergo a 7-day washout period, and crossed over to the alternate treatment (prodrug or placebo) for an additional 14 days. The prodrug-containing and placebo doses were each 1300 mg tablets. The prodrug tablet contained 600 mg of the prodrug and 700 mg of various diluents, tableting lubricants and a surfactant. The placebo tablets also weighed 1300 mg, contained no prodrug, and contained correspondingly higher amounts of diluents, lubricants and the surfactant. The dosing was as follows. Patients were started on a dose of 600 mg of prodrug, taken in the evening, and titrated up to a maximum of 1800 mg of prodrug. All patients had assessments taken of their RLS symptom severity and sleep quality before starting the treatments to set a baseline level for comparison against the placebo and drug arms of the study. The RLS symptoms were rated using the International RLS Study Group Diagnostic Criteria, a questionnaire having 10 questions, each with a severity rating of zero to four, and hence a total numerical score range from 0 to 40 with 0-15 being considered mild RLS symptoms, 16-25 being considered moderate RLS symptoms and 26-40 being considered severe RLS symptoms. The quality of a patient's sleep was assessed by having each patient fill out a questionnaire and by videotaping each patient during sleep and then having a technician view the videotape and count the number of periodic limb movements.

It will be apparent to those skilled in the art that many modifications, both to materials and methods, may be practiced without departing from the scope of this disclosure. Accordingly, the present embodiments are to be considered as illustrative and not restrictive, and the invention is not to be limited to the details given herein, but may be modified within the scope and equivalents of the allowed claims.

All publications and patents cited herein are incorporated by reference in their entirety.

The invention claimed is:

1. A method of treating restless legs syndrome in a patient, comprising orally administering to the patient in need of such treatment a sustained release dosage form containing a therapeutically effective amount of 1-{[(α-isobutanoyloxyethoxy) carbonyl]-aminomethyl}-1-cyclohexane acetic acid or a pharmaceutically acceptable salt, hydrate or solvate thereof.

2. A method of improving sleep in a patient with restless legs syndrome, comprising orally administering to the patient in need of such treatment a sustained release dosage form containing a therapeutically effective amount of 1-{[(α-isobutanoyloxyethoxy)carbonyl]-aminomethyl}-1-cyclohexane acetic acid or a pharmaceutically acceptable salt, hydrate or solvate thereof.

3. The method of claim 1, wherein the restless legs syndrome is idiopathic.

4. The method of claim 1, wherein the restless legs syndrome is secondary to a medical condition.

5. The method of claim 4, wherein the medical condition is iron deficiency.

6. The method of claim 4, wherein the medical condition requires dialysis.

7. The method of claim 1, wherein the patient suffers symptoms of restless legs syndrome while awake and inactive.

8. The method of claim 1, wherein the patient suffers symptoms of restless legs syndrome while asleep.

9. The method of claim 1, wherein the dosage form provides a therapeutic concentration of 1-(aminomethyl)cyclohexane acetic acid in the plasma of the patient for a period of at least about 6 hours.

10. The method of claim 1, wherein the dosage form comprises an osmotic dosage form, a prodrug-releasing polymer, a prodrug-releasing lipid, a prodrug-releasing wax, tiny timed-release pills or prodrug releasing beads.

11. The method of claim 1, wherein the 1-{[(α-isobutanoyloxyethoxy)carbonyl]-aminomethyl}-1-cyclohexane acetic acid or a pharmaceutically acceptable salt, hydrate or solvate thereof is 1-{[(α-isobutanoyloxyethoxy)carbonyl]aminomethyl}-1-cyclohexane acetic acid.

12. The method of claim 1, wherein the 1-{[(α-isobutanoyloxyethoxy)carbonyl]-aminomethyl}-1 -cyclohexane acetic acid or a pharmaceutically acceptable salt, hydrate or solvate thereof is 1-{[(α-isobutanoyloxyethoxy)carbonyl]-aminomethyl}-1-cyclohexane acetic acid or a pharmaceutically acceptable salt thereof.

13. The method of claim 1, wherein the sustained release oral dosage form is administered in an amount of about 600 mg/dose.

14. The method of claim 13, wherein the dose is administered during the evening.

15. A method of treating restless legs syndrome in a patient, comprising orally administering to the patient in need of such treatment a sustained release dosage form containing a therapeutically effective amount of 1-{[(α-isobutanoyloxyethoxy) carbonyl]-aminomethyl}-1-cyclohexane acetic acid or a pharmaceutically acceptable salt, hydrate or solvate thereof in an amount of between 100 mg/dose to 1000 mg/dose with up to 4 doses administered per day.

16. A method of improving sleep in a patient with restless legs syndrome, comprising orally administering to the patient in need of such treatment a sustained release dosage form containing a therapeutically effective amount of 1-{[(α-isobutanoyloxyethoxy)carbonyl]-aminomethyl}-1-cyclohexane acetic acid or a pharmaceutically acceptable salt, hydrate or solvate thereof in an amount of between 100 mg/dose to 1000 mg/dose with up to 4 doses administered per day.

17. The method of claim 15, wherein the restless legs syndrome is idiopathic.

18. The method of claim 15, wherein the restless legs syndrome is secondary to a medical condition.

19. The method of claim 18, wherein the medical condition is iron deficiency.

20. The method of claim 18, wherein the medical condition requires dialysis.

21. The method of claim 15, wherein the patient suffers symptoms of restless legs syndrome while awake and inactive.

22. The method of claim 15, wherein the patient suffers symptoms of restless legs syndrome while asleep.

23. The method of claim 15, wherein the dosage form provides a therapeutic concentration of 1-(aminomethyl)cyclohexane acetic acid in the plasma of the patient for a period of at least about 6 hours.

24. The method of claim 15, wherein the dosage form comprises an osmotic dosage form, a prodrug-releasing polymer, a prodrug-releasing lipid, a prodrug-releasing wax, tiny timed-release pills or prodrug releasing beads.

25. The method of claim 15, wherein the 1-{[(α-isobutanoyloxyethoxy)carbonyl]-aminomethyl}-1-cyclohexane acetic acid or a pharmaceutically acceptable salt, hydrate or solvate thereof is 1-{[(α-isobutanoyloxyethoxy)carbonyl]-aminomethyl}-1-cyclohexane acetic acid.

26. The method of claim 15, wherein the 1-{[(α-isobutanoyloxyethoxy)carbonyl]-aminomethyl}-1-cyclohexane acetic acid or a pharmaceutically acceptable salt, hydrate or solvate thereof is 1-{[(α-isobutanoyloxyethoxy)carbonyl]-aminomethyl}-1-cyclohexane acetic acid or a pharmaceutically acceptable salt thereof.

27. The method of claim 15, wherein a dose is about 600 mg.

28. The method of claim 27, wherein the dose is administered during the evening.

29. The method of claim 2, wherein the restless legs syndrome is idiopathic.

30. The method of claim 2, wherein the restless legs syndrome is secondary to a medical condition.

31. The method of claim 30, wherein the medical condition is iron deficiency.

32. The method of claim 30, wherein the medical condition requires dialysis.

33. The method of claim 2, wherein the patient suffers symptoms of restless legs syndrome while awake and inactive.

34. The method of claim 2, wherein the patient suffers symptoms of restless legs syndrome while asleep.

35. The method of claim 2, wherein the dosage form provides a therapeutic concentration of 1-(aminomethyl)cyclohexane acetic acid in the plasma of the patient for a period of at least about 6 hours.

36. The method of claim 2, wherein the dosage form comprises an osmotic dosage form, a prodrug-releasing polymer, a prodrug-releasing lipid, a prodrug-releasing wax, tiny timed-release pills or prodrug releasing beads.

37. The method of claim 2, wherein the 1-{[(α-isobutanoyloxyethoxy)carbonyl]-aminomethyl}-1-cyclohexane acetic acid or a pharmaceutically acceptable salt, hydrate or solvate thereof is 1-{[(α-isobutanoyloxyethoxy)carbonyl]-aminomethyl}-1-cyclohexane acetic acid.

38. The method of claim 2, wherein the 1-{[(α-isobutanoyloxyethoxy)carbonyl]-aminomethyl}-1-cyclohexane acetic acid or a pharmaceutically acceptable salt, hydrate or solvate thereof is 1-{[(α-isobutarioyloxyethoxy)carbonyl]-aminomethyl}-1-cyclohexane acetic acid or a pharmaceutically acceptable salt thereof.

39. The method of claim 2, wherein the sustained release oral dosage form is administered in an amount of about 600 mg/dose.

40. The method of claim 39, wherein the dose is administered during the evening.

41. The method of claim 16, wherein the restless legs syndrome is idiopathic.

42. The method of claim 16, wherein the restless legs syndrome is secondary to a medical condition.

43. The method of claim 42, wherein the medical condition is iron deficiency.

44. The method of claim 42, wherein the medical condition requires dialysis.

45. The method of claim 16, wherein the patient suffers symptoms of restless legs syndrome while awake and inactive.

46. The method of claim 16, wherein the patient suffers symptoms of restless legs syndrome while asleep.

47. The method of claim 16, wherein the dosage form provides a therapeutic concentration of 1-(aminomethyl)cyclohexane acetic acid in the plasma of the patient for a period of at least about 6 hours.

48. The method of claim 16, wherein the dosage form comprises an osmotic dosage form, a prodrug-releasing polymer, a prodrug-releasing lipid, a prodrug-releasing wax, tiny timed-release pills or prodrug releasing beads.

49. The method of claim 16, wherein the 1-{[(α-isobutanoyloxyethoxy)carbonyl]-aminomethyl}-1-cyclohexane acetic acid or a pharmaceutically acceptable salt, hydrate or solvate thereof is 1-{[(α-isobutarioyloxyethoxy)carbonyl]-aminomethyl}-1-cyclohexane acetic acid.

50. The method of claim 16, wherein the 1-{[(α-isobutanoyloxyethoxy)carbonyl]-aminomethyl}-1-cyclohexane acetic acid or a pharmaceutically acceptable salt, hydrate or solvate thereof is 1-{[(α-isobutarioyloxyethoxy)carbonyl]-aminomethyl}-1-cyclohexane acetic acid or a pharmaceutically acceptable salt thereof.

51. The method of claim 16, wherein a dose is about 600 mg.

52. The method of claim 51, wherein the dose is administered during the evening.

* * * * *

UNITED STATES PATENT AND TRADEMARK OFFICE
CERTIFICATE OF CORRECTION

| | |
|---|---|
| PATENT NO. | : 8,114,909 B2 |
| APPLICATION NO. | : 10/969196 |
| DATED | : February 14, 2012 |
| INVENTOR(S) | : Ronald W. Barrett et al. |

It is certified that error appears in the above-identified patent and that said Letters Patent is hereby corrected as shown below:

In column 48, at line 17, delete "thereof is 1-{[(α-isobutarioyloxyethoxy)carbonyl]-aminom-" and insert --thereof is 1-{[(α-isobutanoyloxyethoxy)carbonyl]-aminom- --.

In column 48, at line 48, delete "solvate thereof is 1-{[(α-isobutarioyloxyethoxy)carbonyl]-" and insert --solvate thereof is 1-{[(α-isobutanoyloxyethoxy)carbonyl]- --.

In column 48, at line 53, delete "solvate thereof is 1-{[(α-isobutarioyloxyethoxy)carbonyl]-" and insert --solvate thereof is 1-{[(α-isobutanoyloxyethoxy)carbonyl]- --.

Signed and Sealed this
Twenty-fifth Day of December, 2012

David J. Kappos
*Director of the United States Patent and Trademark Office*